(12) United States Patent
Yan et al.

(10) Patent No.: US 9,738,615 B2
(45) Date of Patent: Aug. 22, 2017

(54) CYCLOPHILIN D INHIBITORS

(71) Applicant: The University of Kansas, Lawrence, KS (US)

(72) Inventors: Shirley ShiDu Yan, Leawood, KS (US); Koteswara Rao Valasani, Kadapa (IN)

(73) Assignee: The University of Kansas, Lawrence, KS (US)

(*) Notice: Subject to any disclaimer, the term of this patent is extended or adjusted under 35 U.S.C. 154(b) by 0 days.

(21) Appl. No.: 14/851,835

(22) Filed: Sep. 11, 2015

(65) Prior Publication Data

US 2016/0075669 A1  Mar. 17, 2016

Related U.S. Application Data

(60) Provisional application No. 62/049,101, filed on Sep. 11, 2014.

(51) Int. Cl.
 A61K 31/426 (2006.01)
 C07D 277/56 (2006.01)
 C07D 513/04 (2006.01)

(52) U.S. Cl.
 CPC ......... *C07D 277/56* (2013.01); *C07D 513/04* (2013.01)

(58) Field of Classification Search
 CPC .................................................. C07D 277/56
 See application file for complete search history.

(56) References Cited

PUBLICATIONS

Structure Based Design, Synthesis, Pharmacophore Modeling, Virtual Screening, and Molecular Docking Studies for Identification of Novel Cyclophilin D Inhibitors, Valasani et al.J. Chem. Inf. Model., 2014, 54 (3), pp. 902-912.*

* cited by examiner

*Primary Examiner* — Brian McDowell
(74) *Attorney, Agent, or Firm* — Maschoff Brennan

(57) ABSTRACT

A compound that can function as a Cyclophilin D can include a structure of Formula 1 or Formula 2 or Formula 3 or Formula 4 or Formula 5 or Formula 6 or Formula 7 or Formula 8, derivative thereof, prodrug thereof, salt thereof, or stereoisomer thereof, or having any chirality at any chiral center, or tautomer, polymorph, solvate, or combination thereof, as presented herein. The Cyclophilin D inhibitors can inhibit onset or treat neurodegenerative disease, such as Alzheimer's disease, or can be used for inhibiting progression or treating diabetes. An example of such a compound is provided by Formula 1A Formula 1A

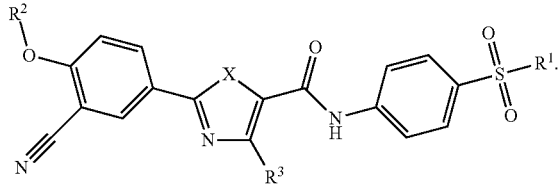

15 Claims, 14 Drawing Sheets

CYCLOPHILIN D INHIBITORS

CROSS-REFERENCE

This patent application claims priority to U.S. Provisional Application No. 62/049,101 filed Sep. 11, 2014, which provisional is incorporated herein by specific reference in its entirety.

GOVERNMENT RIGHTS

This invention was made with government support under R37AG037319 and R01GM095355 awarded by the National Institutes of Health. The government has certain rights in the invention.

BACKGROUND

Alzheimer's disease (AD) is a chronic neurodegenerative disease that primarily affects the elderly and for which there are currently only symptomatic treatments. Early pathological features of the AD brain include mitochondrial and synaptic dysfunction, which is considered to be related to progressive amyloid-beta (Aβ) oligomer accumulation in synaptic mitochondria. This affects membrane potential, membrane permeability transition pore (mPTP) formation, respiration, energy metabolism, oxidative stress, mitochondrial dynamics and calcium homeostasis. Since mitochondrial dysfunction is believed to play a role in Aβ-induced toxicity, a compound that restores this dysfunction might have potential therapeutic benefit. Thus, Aβ oligomer inhibitors or procedures for blocking Aβ oligomer production appear to offer promising approaches for prevention and treatment of AD. Cyclophilin D (CypD), a peptidyl prolyl isomerase F, resides in the mitochondrial matrix, associates with the inner mitochondrial membrane and plays a central role in opening the mitochondrial mPTP leading to cell death. Neurons in AD-affected regions of the brain have significantly elevated levels of CypD.

Therefore, it may be advantageous to inhibit CypD in order to inhibit the effects of and provide treatments for AD. CypD is also known to positively effects of diabetes.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1A:
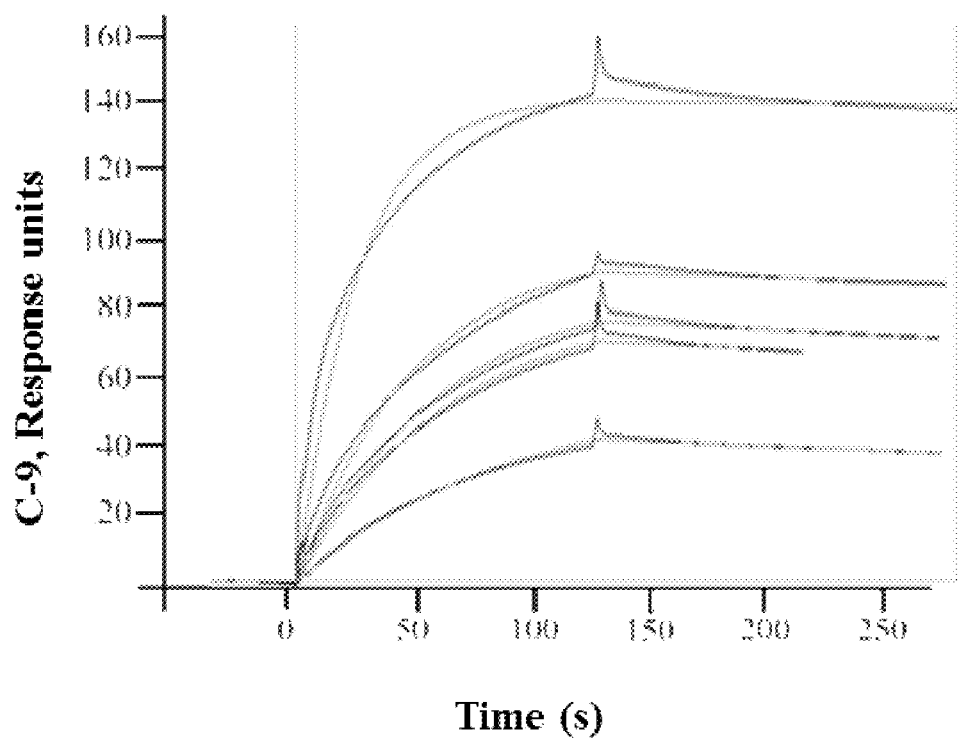
FIG. 1A includes a graph that shows that the CypD inhibitor Compound 9 binds to immobilized CypD in a dose-dependent manner.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Generally, the present technology relates to inhibitors of Cyclophilin D (CypD) and methods of use thereof. The inhibitors can be included in pharmaceutical compositions and administered to inhibit onset or progression of a neurodegenerative disease, such as Alzheimer's disease (AD). Also, the CypD inhibitors can be used to treat diabetes. The inhibitors can be used to inhibit opening of the mitochondrial membrane permeability transition pore, and lead to cell death. The inhibitors can inhibit CypD from associating with the inner mitochondrial membrane, inhibit interactions with amyloid beta to inhibit mitochondrial and neuronal stress, and to inhibit development or progression of AD as well as to treat AD. The CypD inhibitors can also be used to inhibit development or progression of AD as well as to treat AD.

It has been found that the biological activity of two families of small-molecule CypD inhibitors (e.g., C-6 Family and C-9 Family) can bind to CypD and attenuate mitochondrial and cellular perturbations that are caused by Aβ and calcium stress. It has been determined that these small molecule CypD inhibitors may serve as drugs for the prevention and treatment of neurodegenerative diseases including AD. The CypD inhibitors may also be used to treat diabetes and diabetes induced complications. In part, this is because the CypD inhibitors can have higher solubility, better ability to cross the blood brain barrier (BBB), lower toxicity, and/or higher cell permeability compared to conventional therapeutics or treatment substances. That is, the drug can be administered directly to a subject in a location other than the brain, and the drug can traverse the BBB.

In one embodiment, the compounds described herein are CypD inhibitors that can be used for the inhibition or treatment of neurodegenerative diseases (e.g., AD). The present technology includes compositions having the CypD inhibitors, methods of synthesis of the CypD inhibitors, and methods of treatment of neurodegenerative diseases with the CypD inhibitors. In one family of compounds, the compounds can be the structures of Formula 1 or their derivatives. In another family of compounds, the compounds can be the structures of Formulae 2-6 or their derivatives. The two families of compounds are provided herein.

The compounds that are CypD inhibitors can include a structure of Formula 1 or Formula 2 or Formula 3 or Formula 4 or Formula 5 or Formula 6 or Formula 7 or Formula 8, derivative thereof, prodrug thereof, salt thereof, or stereoisomer thereof, or having any chirality at any chiral center, or tautomer, polymorph, solvate, or combination thereof:

Formula 1

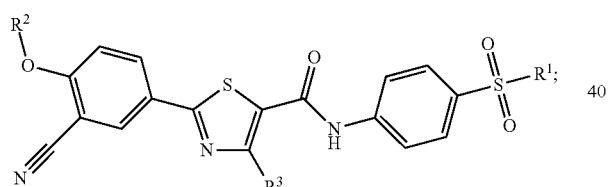

Formula 2

Formula 3

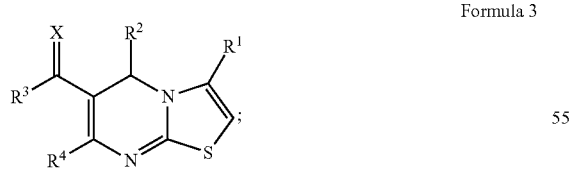

Formula 4

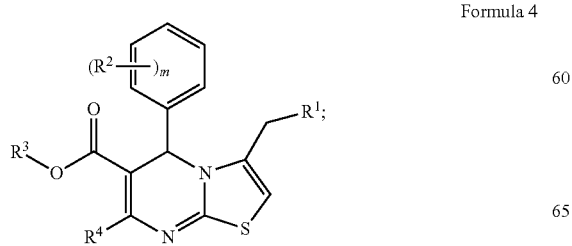

Formula 5

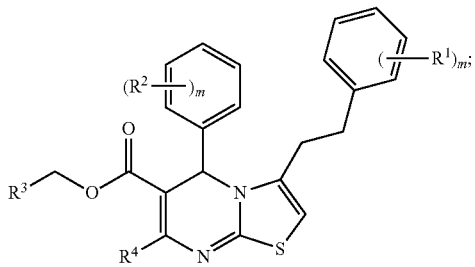

Formula 6

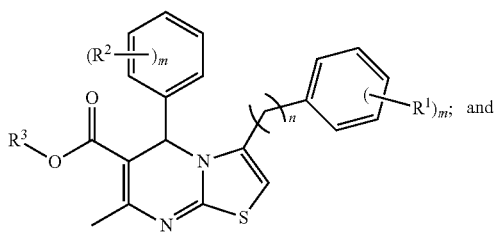

Formula 7

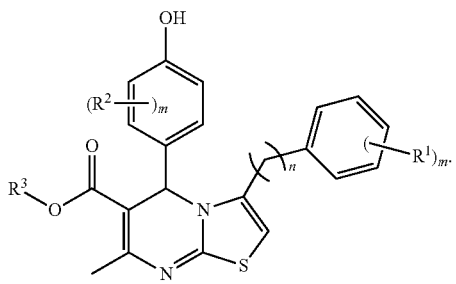

Formula 8

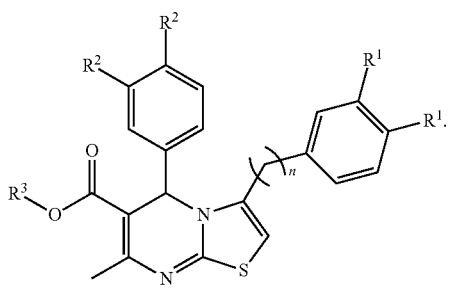

In the Formula 1-8 any of the R groups can be independently any substituents; X can be S or O; n is 0 or an integer and S in the rings can be replaced with O. When on a ring, such as an aryl (e.g., benzene), the R groups can be on any of the carbons, such as an R group on one, two, three, four or five carbons, or more preferably on one or two carbons, such as in Formula 4, 5, and 6, whereby m is 0 1, 2, 3, 4 or 5, preferably 0, 1 or 2.

In one embodiment, in the Formula 1-8, any one or more of $R^1$, $R^2$, $R^3$, or $R^4$ are independently any substituent; X can be S or O; and S in the rings can be replaced with O. In one aspect, any one or more of $R^1$, $R^2$, $R^3$, or $R^4$ are independently any substituent that maintains functionality as a CypD inhibitor. Any one or more of $R^1$ or $R^2$ can be on any of the carbons of the rings, such as an $R^1$ or $R^2$ group on one, two, three, four or five carbons, or more preferably on one or two carbons, such as in Formula 4, 5, 6, 7 and 8. An example with the S in the rings being replaced by O is shown below with Formula 1A having the X, which can thereby be S or O.

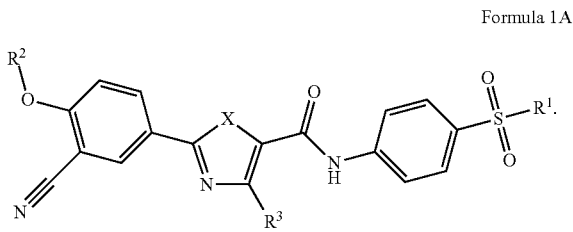

Formula 1A

In one embodiment, in the Formula 1-8, any one or more of $R^1$, $R^2$, $R^3$, or $R^4$ are independently any one or more of the substituents selected from the group of hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl (including $C_2$-$C_{24}$ alkylcarbonyl (—CO-alkyl) and $C_7$-$C_{20}$ arylcarbonyl (—CO-aryl)), acyloxy (—O-acyl), $C_2$-$C_{24}$ alkoxycarbonyl (—(CO)—O-alkyl), $C_7$-$C_{20}$ aryloxycarbonyl (—(CO)—O-aryl), halocarbonyl (—(CO)—X where X is halo), $C_2$-$C_{24}$ alkylcarbonato (—O—(CO)—O-alkyl), $C_7$-$C_{20}$ arylcarbonato (—O—(CO)—O-aryl), carboxy (—COOH), carboxylato (—COO), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), di-substituted arylcarbamoyl (—(CO)—NH-aryl)$_2$, thiocarbamoyl (—(CS)—NH$_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-substituted arylthiocarbamoyl (—(CS)—NH-aryl), di-substituted arylthiocarbamoyl (—(CS)—NH-aryl)$_2$, carbamido (—NH—(CO)—NH$_2$), mono-($C_1$-$C_{24}$ alkyl)-substituted carbamido (—NH—(CO)—NH($C_1$-$C_{24}$ alkyl)), di-($C_1$-$C_{24}$ alkyl)-substituted carbamido (—NH(CO)—N($C_1$-$C_{24}$ alkyl)$_2$), mono-substituted aryl carbamido (—NH—(CO)—NH-aryl), di-substituted aryl carbamido (—NH—(CO)—N-(aryl)$_2$) cyano(—C≡N), isocyano (—N$^+$≡C$^-$), cyanato (—O—C≡C$^-$), isocyanato (—O—N$^+$≡C$^-$), thiocyanato (—S—C≡N), isothiocyanato (—S—N$^+$≡C$^-$), azido (—N=N$^+$=N$^-$), formyl (—(CO)—H), thioformyl (—(CS)—H), amino (—NH$_2$), mono- and di-($C_1$-$C_{24}$ alkyl)-substituted amino, mono- and di-($C_6$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R is hydrogen, $C_1$-$C_{24}$ alkyl, $C_6$-$C_{20}$ aryl, $C_7$-$C_{24}$ alkaryl, $C_7$-$C_{24}$ aralkyl, etc.), alkylimino (—CR=N(alkyl), where R=hydrogen, $C_1$-$C_{24}$ alkyl, aryl, alkaryl, aralkyl, etc.), arylimino (—CR=N(aryl), where R=hydrogen, alkyl, aryl, alkaryl, etc.), nitro (—NO$_2$), nitroso (—NO), sulfonic acid (—SO$_2$—OH), sulfonato (—SO$_2$—O$^-$), $C_1$-$C_{24}$ alkylsulfanyl (—S-alkyl; also termed "alkylthio"), $C_6$-$C_{20}$ arylsulfanyl (—S-aryl; also termed "arylthio"), $C_1$-$C_{24}$ alkylsulfinyl (—(SO)-alkyl), $C_6$-$C_{20}$ arylsulfinyl (—(SO)-aryl), $C_1$-$C_{24}$ alkylsulfonyl (—SO$_2$-alkyl), $C_6$-$C_{20}$ arylsulfonyl (—SO$_2$-aryl), phosphono (—P(O)(OH)$_2$), phosphonato (—P(O)(O$^-$)$_2$), phosphinato (—P(O)(O—)), phospho (—PO$_2$), phosphino (—PH$_2$), any with or without hetero atoms (e.g., N, O, P, S, or other) where the hetero atoms can be substituted (e.g., hetero atom substituted for carbon in chain or ring) for the carbons or in addition thereto (e.g., hetero atom added to carbon chain or ring) swapped, derivatives thereof, and combinations thereof.

In one embodiment, in Formula 1, the substituents are any one or more of: $R^1$ being straight or branched alkyl or aryl substituted or unsubstituted, alkoxy, amine or hydroxyl, $R^2$ being straight or branched alkyl or aryl substituted or unsubstituted; $R^3$ being straight or branched alkyl or aryl substituted or unsubstituted.

In one example of Formula 1, R1 is an amine, R2 is straight or branched alkyl, and R3 is a methyl. The R2 can be methyl, ethyl, propyl, such as isopropyl.

In one embodiment, in Formula 2, the substituents are any one or more of: $R^1$ being an alkylaryl that is substituted or unsubstituted or an aryl that is substituted or unsubstituted, $R^2$ being an alkylaryl that is substituted or unsubstituted or an aryl that is substituted or unsubstituted; $R^3$ being an ester, such as an alkyl ester, and/or $R^4$ is an alkyl.

In one embodiment, in Formula 3, the substituents are any one or more of: $R^1$ being an alkylaryl that is substituted or unsubstituted or an aryl that is substituted or unsubstituted, $R^2$ being an alkylaryl that is substituted or unsubstituted or an aryl that is substituted or unsubstituted; $R^3$ alkoxy, such as methoxy or ethoxy, and/or $R^4$ is an alkyl.

In one embodiment, in Formula 4, 5, 6, 7, or 8 the substituents are any one or more of: $R^1$ and/or $R^2$ independently being hydrogen, $C_1$-$C_{24}$ alkyl, $C_2$-$C_{24}$ alkenyl, $C_2$-$C_{24}$ alkynyl, $C_6$-$C_{20}$ aryl, $C_7$-$C_{24}$ alkaryl, $C_7$-$C_{24}$ aralkyl, halo, hydroxyl, sulfhydryl, $C_1$-$C_{24}$ alkoxy, $C_2$-$C_{24}$ alkenyloxy, $C_2$-$C_{24}$ alkynyloxy, $C_6$-$C_{20}$ aryloxy, acyl, nitro (—NO$_2$), nitroso (—NO), sulfo (—SO$_2$—OH), sulfonate, acyloxy (—O-acyl), $C_2$-$C_{24}$ alkoxycarbonyl (—(CO)—O-alkyl), $C_6$-$C_{20}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-substituted arylcarbamoyl (—(CO)—NH-aryl), cyano(—C$_1$), isocyano (—N$^+$≡C$^-$), cyanato (—O—C≡N), isocyanato (—O—N$^+$≡C$^-$), being an alkylaryl that is substituted or unsubstituted or an aryl that is substituted or unsubstituted; $R^3$ and/or $R^4$ is an alkyl. Any one or more of $R^1$ or $R^2$ can be on any of the carbons of the rings, such as an $R^1$ or $R^2$ group on one, two, three, or four carbons, or more preferably on one or two carbons, such as in Formula 4, 5, 6, 7, and 8.

In one embodiment, the CypD inhibitor is one of the structures shown in Scheme 1, Table A, and Table B below.

In one embodiment, the CypD inhibitor is one of the structures shown in Scheme 2, and Table C below.

The compounds can be formulated with any pharmaceutically acceptable carrier for any administration. The administration can result in systemic compounds that can pass the blood brain barrier.

The compounds can be used in any method of modulating Cyclophilin D by administering the compound to a Cyclophilin D. This can include a method of inhibiting Cyclophilin D by adding the compound to Cyclophilin D. The compounds can be used in any method of rescuing Aβ-mediated mitochondrial dysfunction by adding the compound to Cyclophilin D. The Cyclophilic D can be in vivo, in vitro, or ex vivo. The Cyclophilic D can be administered to any subject, such as a cell or organ or organism having the same, such as a human or other animal.

The CypD inhibitors have sufficient ligand binding affinities to be useful therapeutics, as shown by in vitro SPR binding studies. One CypD inhibitor, Compound 9, rescued mitochondrial function by reducing CypD peptidyl prolyl isomerase enzymatic activity and antagonizing calcium-mediated and Aβ-induced mitochondrial swelling. The Compound 9 also reversed Aβ-induced mitochondrial dysfunction as shown by increased CcO and ATP levels, suggesting protective effects on mitochondrial function for this molecule. Cell viability was checked using MTT reduction assay for SK-N-SH cells treated with $Aβ_{1-42}$ alone and with addition of Compound 9, which showed $Aβ_{1-42}$ alone produces a significant decrease in cell viability, while the addition of Compound 9 protected the cells and exhibited similar reduction of MTT without producing severe toxic effects at either low or high doses in healthy cells. Compared to CsA, Compound 9 is a smaller molecule (molecular weight of C-9: 470 vs. CsA: 1202.61). The other compounds (e.g., C-6 Family and C-9 family) are all expected to have similar functionalities, and to bind human CypD protein, and to inhibit Aβ-induced mitochondrial dysfunction.

Figure 1B:
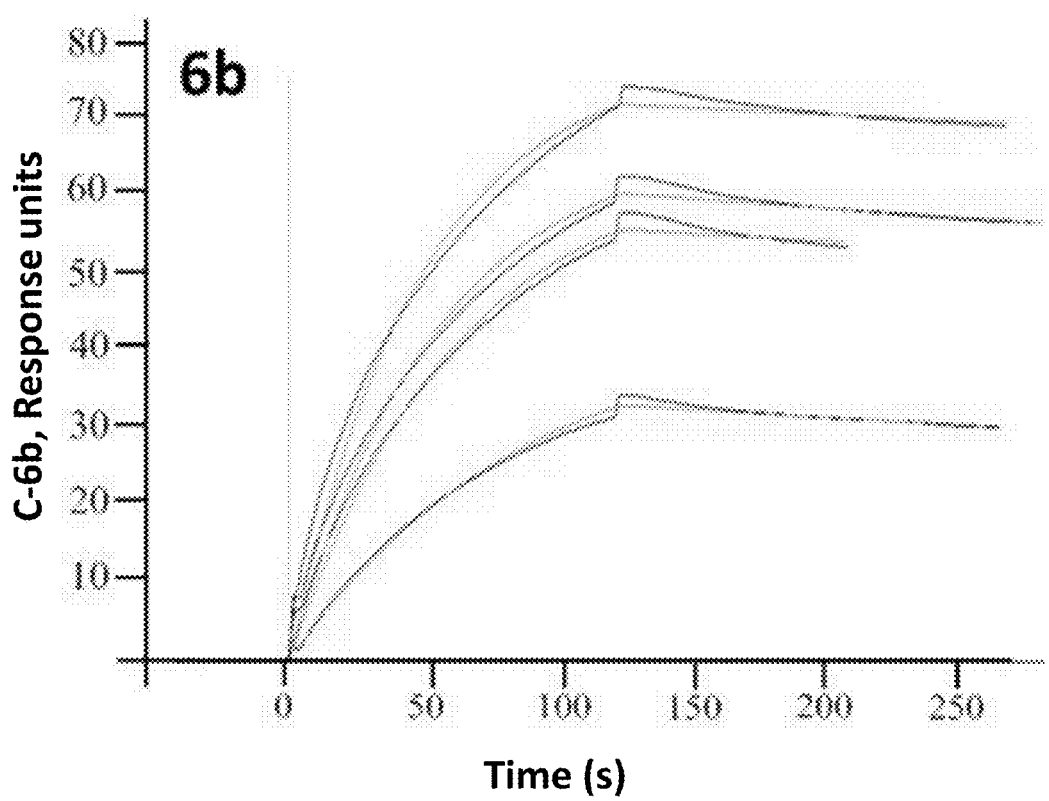
FIG. 1B includes a graph that shows that the CypD inhibitor Compound 6B binds to immobilized CypD in a dose-dependent manner.

Some of the CypD inhibitors shown herein exhibited high binding affinity to human CypD along with the improvement of mitochondrial function, as can be reviewed in the tables and graphs. In vitro SPR was used to verify the ability of the CypD inhibitors to bind to human recombinant CypD protein, which correlates with its potential CypD inhibitory activity. FIGS. 1A-1B demonstrate that some of the synthetic CypD inhibitors (e.g., Compound 9 (C-9) and Compound 6B (C-6b,)) display a high binding affinity for human CypD in a dose dependent manner.

FIGS. 1A-1B show that the synthesized CypD inhibitors each bind to immobilized CypD in a dose-dependent manner. Surface plasmon resonance (SPR) analysis of CypD-Pyrimidine derivative binding interaction, where the globally fit data (black lines) were overlaid with experimental data (greyish lines). Human recombinant CypD protein (10 µg/ml) was immobilized directly on the hydrophilic carboxy methylated dextran matrix of the CM5 sensor chip (Biacore-3000) using the standard primary amine coupling reaction according to standard procedures. Compound 9 (2.5, 5, 10, 15, 20 µM) was injected at a flow rate of 40 µl/min for the determination of the kinetic and equilibrium constants. All data analyses were carried out using BIA evaluation software, and sensor grams were processed by automatic correction for nonspecific bulk refractive index.

The equilibrium dissociation constant ($K_D$) was determined using a 1:1 Langmuir binding fit model and the association ($k_{on}$) and dissociation ($k_{off}$) rate constants were determined using Equations (1) and (2).

$$d_R/d_t = k_{on} \times C \times (R_{max} - R) - k_{off} \times R \quad (1)$$

Where R represents the response unit, C is the concentration of the analyte, and $$K_D = k_{off}/k_{on} \quad (2)$$

The obtained results were evaluated by $\chi^2$ analysis and the kinetic parameters for Compound 9 are provided. The SPR results for Compound 9 and Compound 6B shown in FIGS. 1A-1B clearly indicate that Compound 9 and Compound 6B bind quite strongly to CypD with a $K_D$ value of 149 nM, and Compound 6B has a $K_D$ value of 248 nM.

The ability of CypD inhibitors to inhibit CypD PPIase enzyme activity was determined using a previously utilized "standard" procedure (Kofron, J. L.; Kuzmic, P.; Kishore, V.; Colon-Bonilla, E.; Rich, D. H., Determination of kinetic constants for peptidyl prolyl cis-trans isomerases by an improved spectrophotometric assay. *Biochemistry* 1991, 30, 6127-34). The results are presented in FIGS. 2A-2D and compared to CsA in FIG. 2E.

Figure 8:
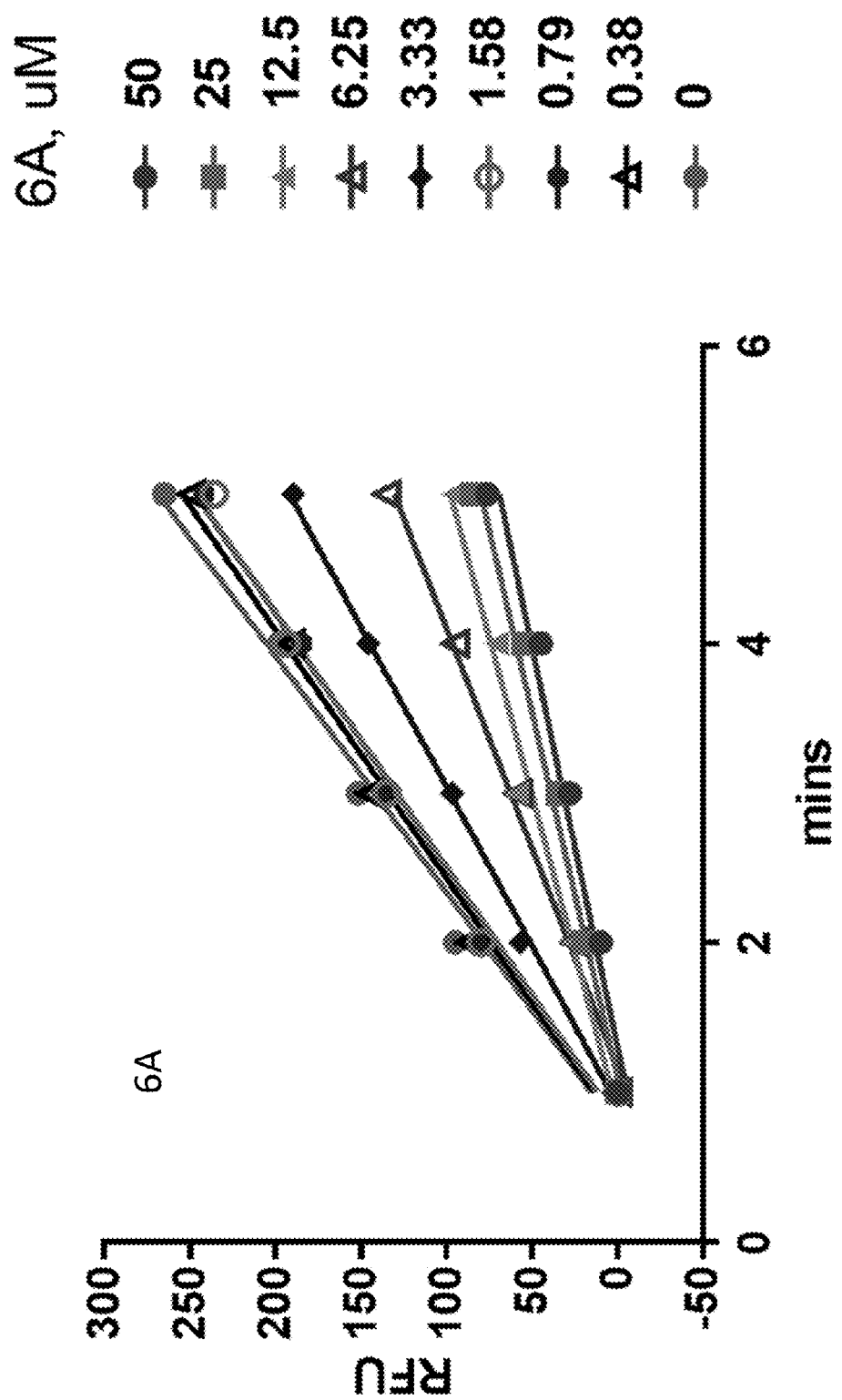
FIG. 8 includes a graph that shows CypD inhibitor Compound 6A inhibiting PPIase activity CypD.
Figure 9:
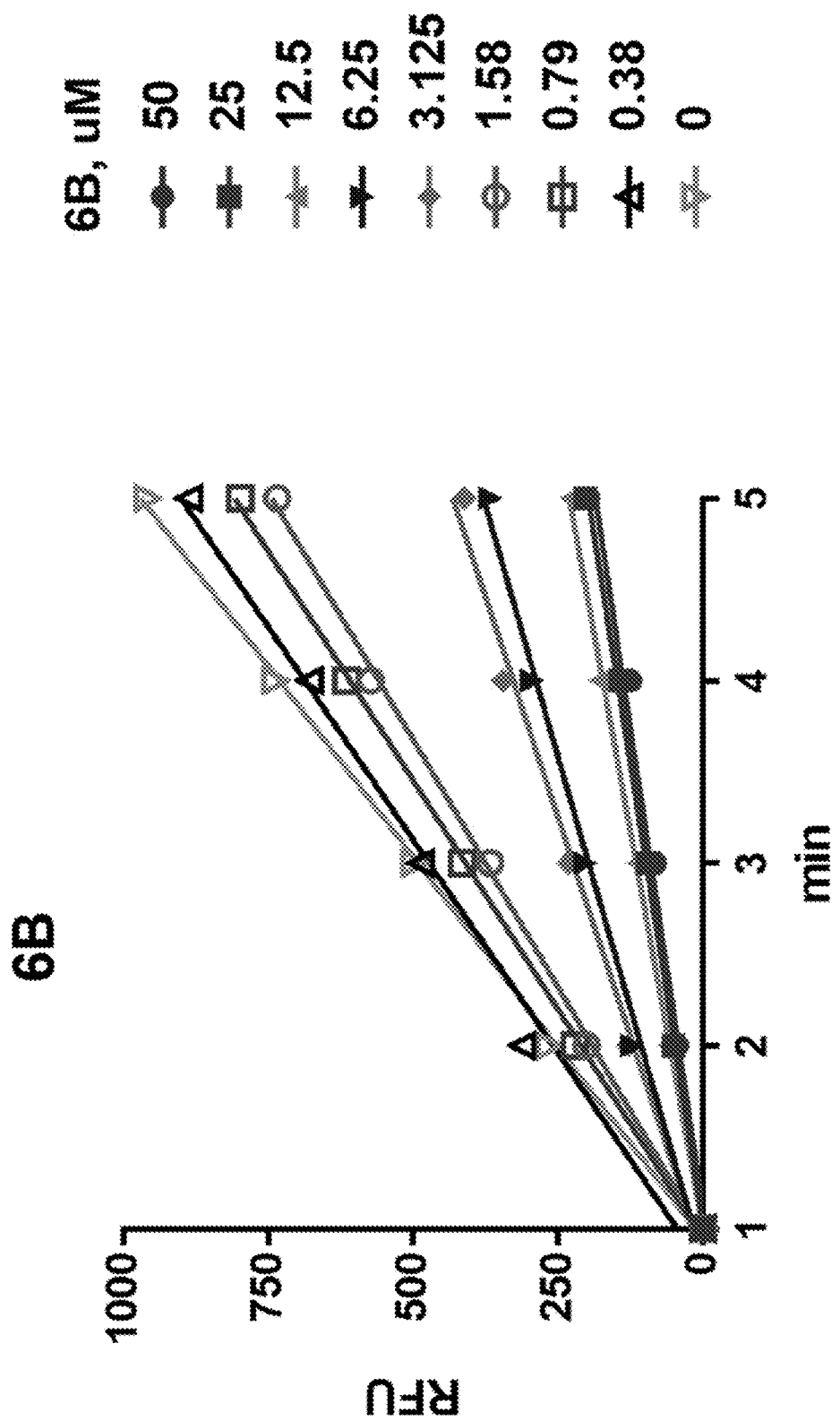
FIG. 9 includes a graph that shows CypD inhibitor Compound 6B inhibiting PPIase activity of CypD.
Figure 10:
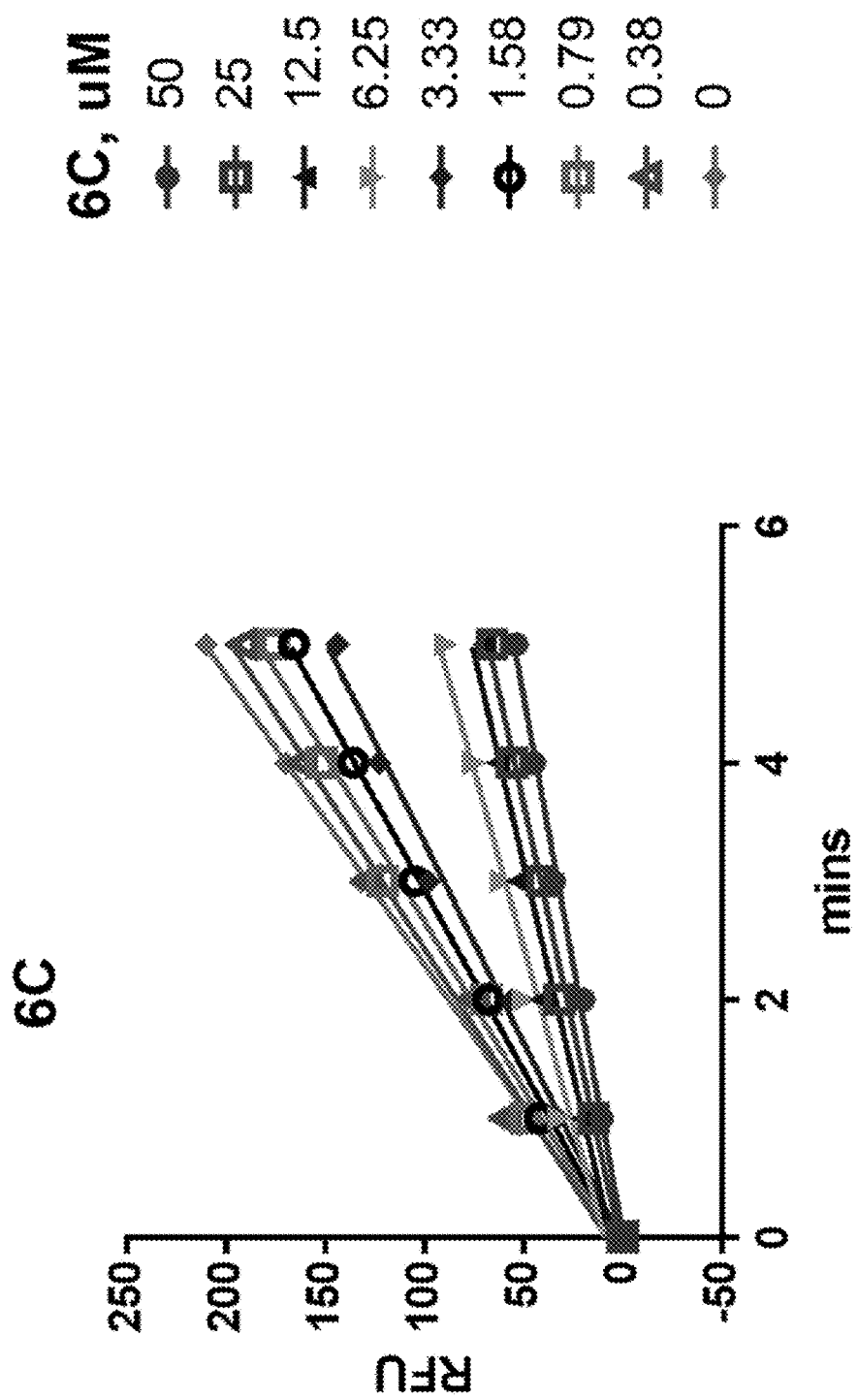
FIG. 10 includes a graph that shows CypD inhibitor Compound 6C inhibiting PPIase activity of CypD.
Figure 11:
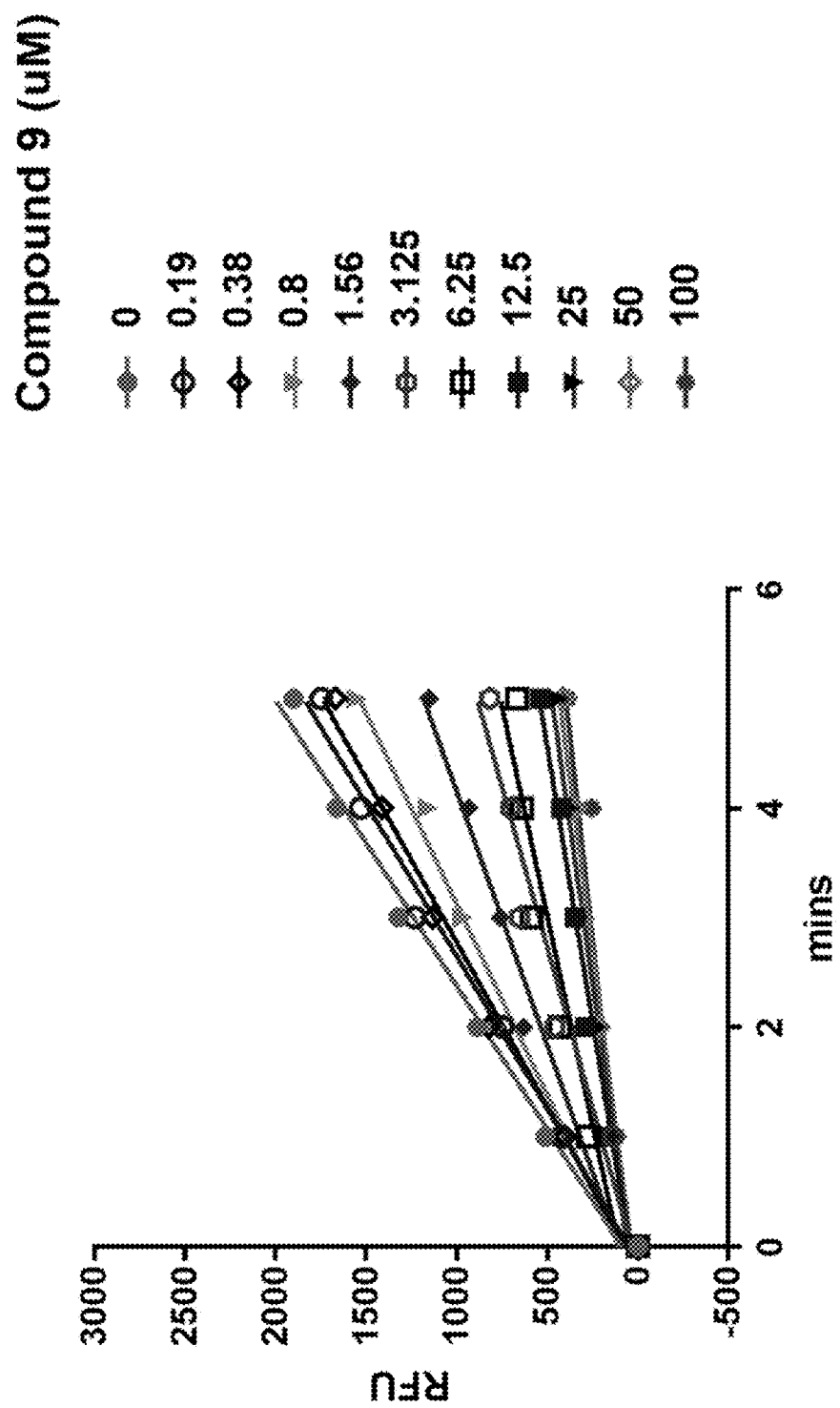
FIG. 11 includes a graph that shows CypD inhibitor Compound 9 inhibiting PPIase activity of CypD.

FIG. 8 shows reaction progress curves collected for CypD activity in DMSO alone or at various Compound 6A concentrations ranging from 0.39 to 50 uM. Linearity was maintained up to 5 minutes of incubation at 25° C. This shows the Compound 6A inhibits CypD activity. FIG. 9 shows reaction progress curves collected for CypD activity in DMSO alone or at various Compound 6B concentrations ranging from 0.39 to 50 uM. Linearity was maintained up to 5 minutes of incubation at 25° C. This shows the Compound 6B inhibits CypD activity. FIG. 10 show reaction progress curves collected for CypD activity in DMSO alone or at various Compound 6C concentrations ranging from 0.39 to 50 uM. Linearity was maintained up to 5 minutes of incubation at 25° C. This shows the Compound 6C inhibits CypD activity. FIG. 11 show reaction progress curves collected for CypD activity in DMSO alone or at various Compound 9 concentrations ranging from 0.19 to 100 uM. Linearity was maintained up to 5 minutes of incubation at 25° C. This shows the Compound 9 inhibits CypD activity.

Figure 2A:
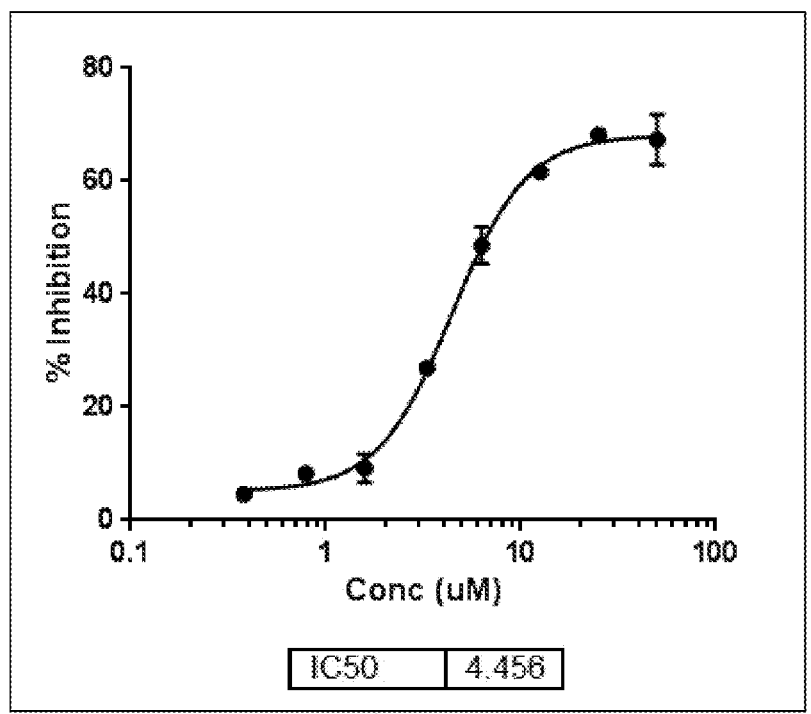
FIG. 2A includes a graph that shows the kinetic analysis of inhibition of CypD by Compound 6A, and shows the IC50 of Compound 6A inhibiting PPIase activity of CypD.
Figure 2B:
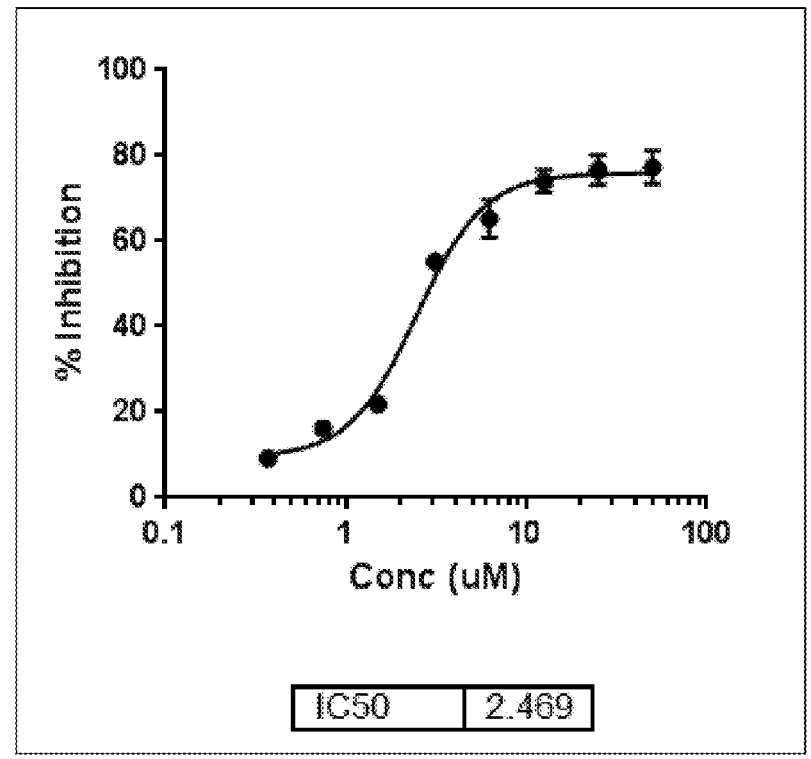
FIG. 2B includes a graph that shows the kinetic analysis of inhibition of CypD by Compound 6B, and shows the IC50 of Compound 6B inhibiting PPIase activity of CypD.
Figure 2C:
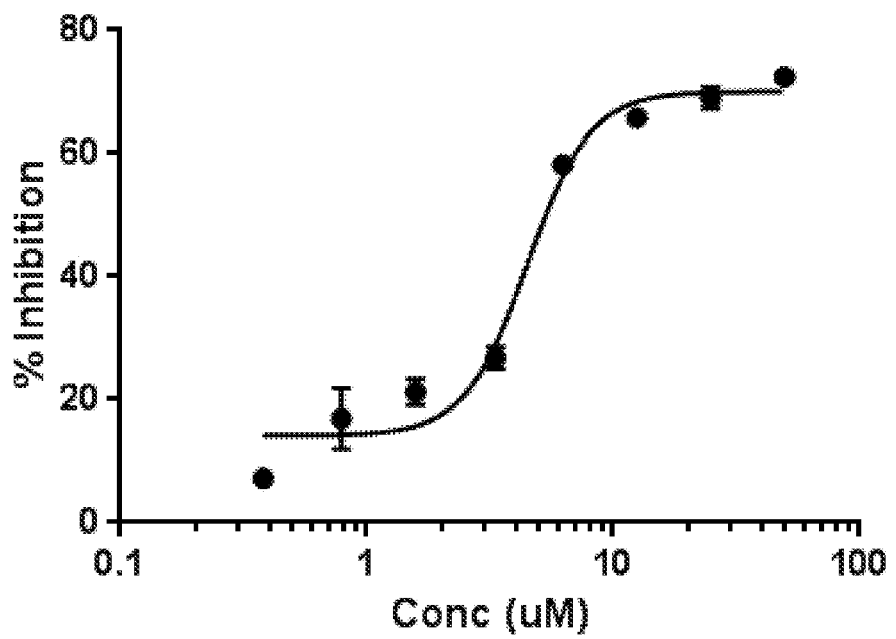
FIG. 2C includes a graph that shows the kinetic analysis of inhibition of CypD by Compound 6C, and shows the IC50 of Compound 6C inhibiting PPIase activity of CypD.
Figure 2D:
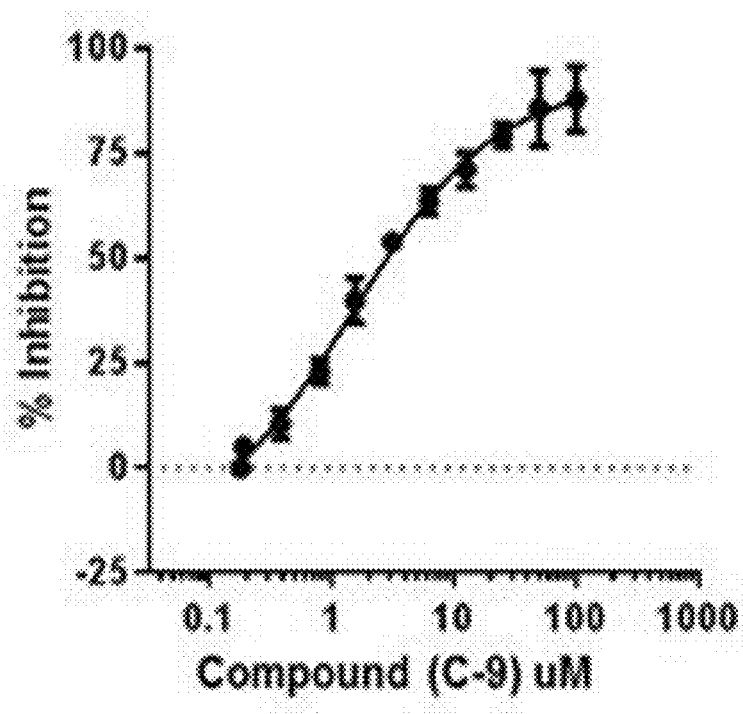
FIG. 2D includes a graph that shows the kinetic analysis of inhibition of CypD by Compound 9, and shows the IC50 of Compound 9 inhibiting PPIase activity of CypD.
Figure 2E:
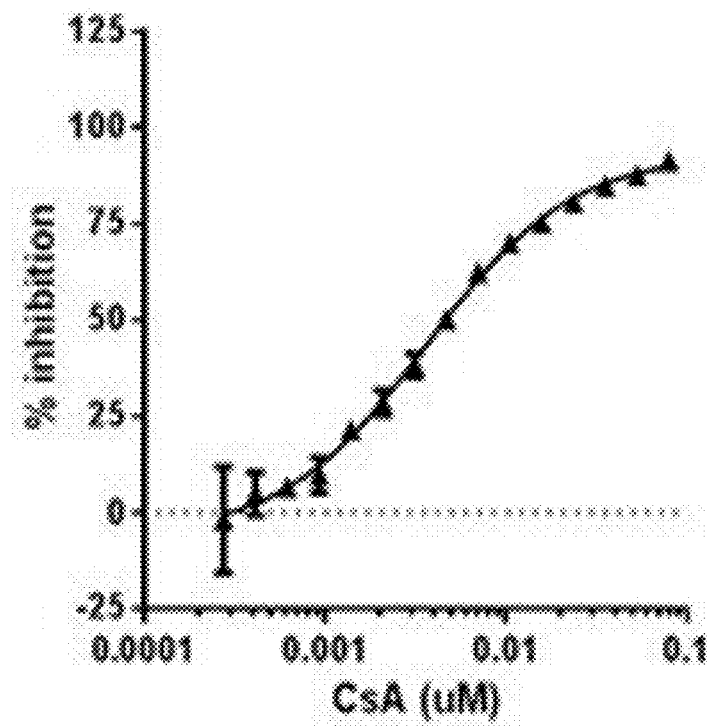
FIG. 2E includes a graph that shows the kinetic analysis of inhibition of CypD by CsA, and shows the IC50 of CsA inhibiting PPIase activity of CypD.

FIG. 2A shows the IC50 of Compound 6A inhibiting PPIase activity of CypD. FIG. 2B shows the IC50 of Compound 6B inhibiting PPIase activity of CypD. FIG. 2C shows the IC50 of compound 6C inhibiting PPIase activity of CypD. FIG. 2D shows the $IC_{50}$ of compound C-9 (i.e., Compound 9) inhibiting PPIase activity of CypD. FIG. 2E shows the $IC_{50}$ of CsA inhibiting PPIase activity of CypD, each of FIGS. 2A-2E being performed with a real-time kinetics assay and calculated using non-linear regression analysis in Graphpad Prism 5.0.

The $IC_{50}$ value for Compound 9 by-real time fluorescence monitoring is 1.49±0.20 µM. Since inhibition of CypD PPIase activity was essential for potentiation of Aβ cytotoxicity, Aβ-induced cytotoxicity can presumably be decreased if the Aβ-CypD interaction is blocked with small-molecule inhibitors like Compound 9.

Figure 3:
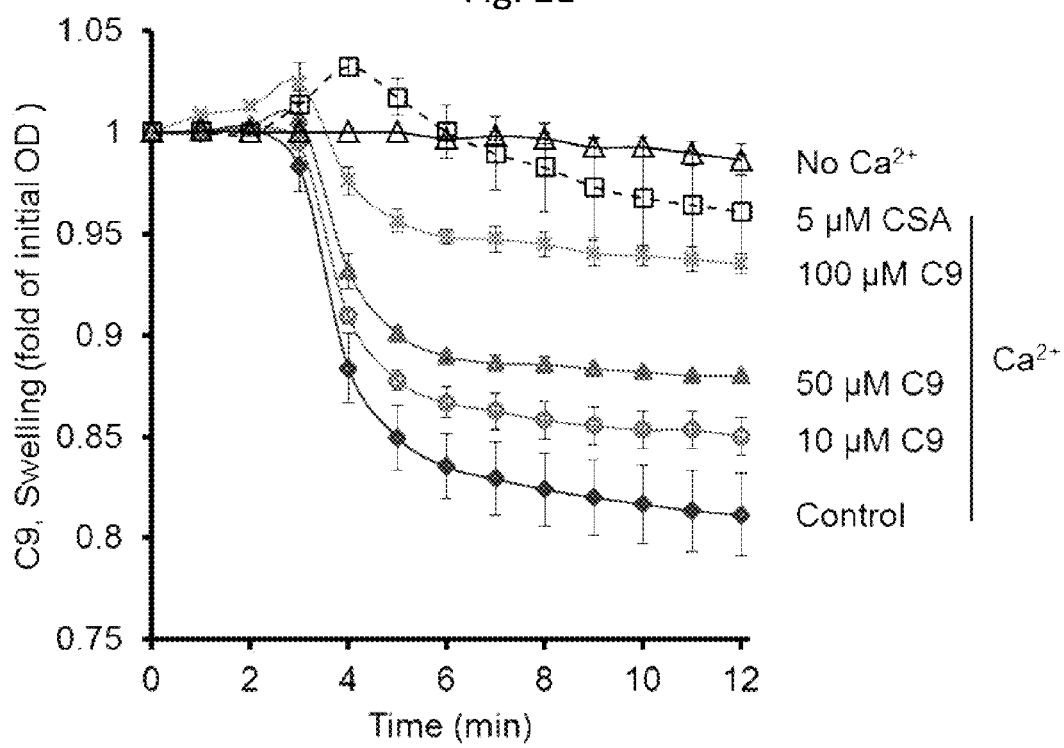
FIG. 3 includes a graph that shows CypD inhibitor Compound 9 reduced calcium-induced mitochondrial swelling.

Mitochondrial swelling in response to calcium was also studied. It is known that CypD-deficient cortical mitochondria are resistant to Aβ- and calcium ($Ca^{2+}$)-induced mitochondrial swelling and mitochondrial permeability transition. These deficient mitochondria also exhibit increased calcium buffering capacity and generate fewer mitochondrial reactive oxygen species. In order to determine the relationship between $Ca^{2+}$ and mitochondrial swelling, cortical mitochondria were isolated from mice and subjected to a swelling assay. Mitochondria treated with $Ca^{2+}$ experienced excessive swelling. However, when Compound 9 was added to the mitocchondria in a dose-dependent manner, swelling was diminished. FIG. 3 includes a graph that shows CypD inhibitor Compound 9 reduced calcium-induced mitochondrial swelling.

The fact that brain mitochondrial swelling was not affected by the inhibitors alone implies a symbiotic relationship between $Ca^{2+}$ and the inhibitor.

Figure 4:
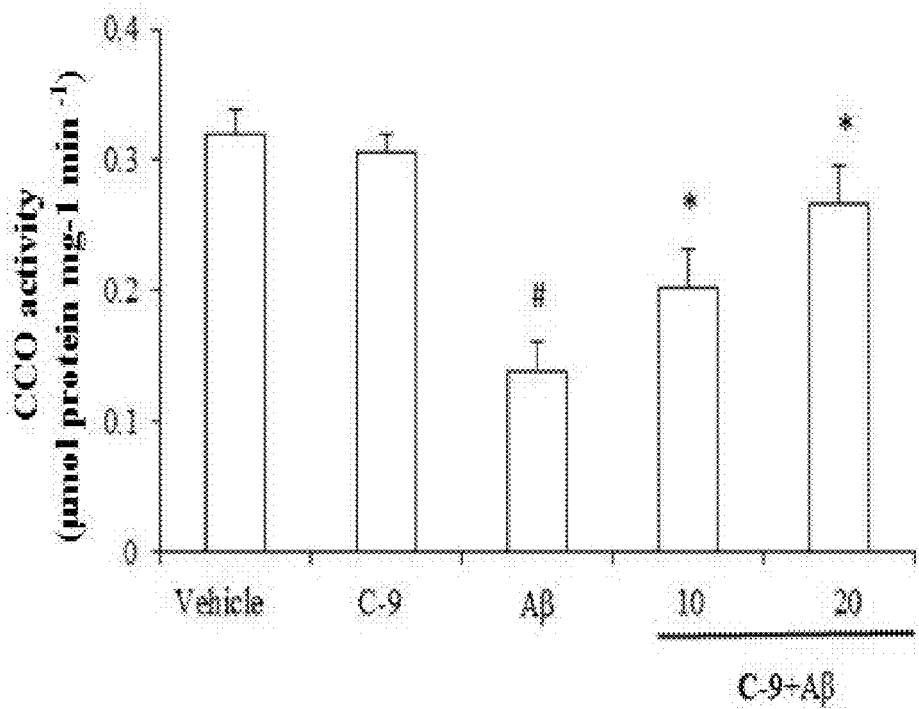
FIG. 4 includes a graph that shows CypD inhibitor Compound 9 revives the Aβ-induced reduction in CcO activity.

The effect of the CypD inhibitors on cytochrome c oxidase (CcO) was studied. The effect of the CypD inhibitors on Aβ-induced mitochondrial respiratory function was assessed by determining cytochrome c oxidase (CcO) activity. CcO is a vital enzyme associated with the mitochondrial electron transport chain. SK-N-SH cells were treated for 48 hours with 5 µM of oligomer $Aβ_{1-42}$ in the presence of 10-20 µM of CypD inhibitor C-9, after which samples were tested for CcO enzyme activity levels. $Aβ_{1-42}$ treatment significantly decreased CcO activity; the addition of CypD inhibitor Compound 9 rescued CcO activity in Aβ-treated cells compared to vehicle-treated cells is shown in FIG. 4. Treating cells with inhibitors alone had no effect on CcO activity in the absence of $A\beta_{1-42}$, demonstrating that the CypD inhibitors do not disrupt normal cell functioning. These results provide evidence that inhibition of CypD rescues CcO activity in Aβ-affected cells without harming healthy cells, suggesting that they are desirable candidates for continued study in AD research and treatment.

Figure 5:
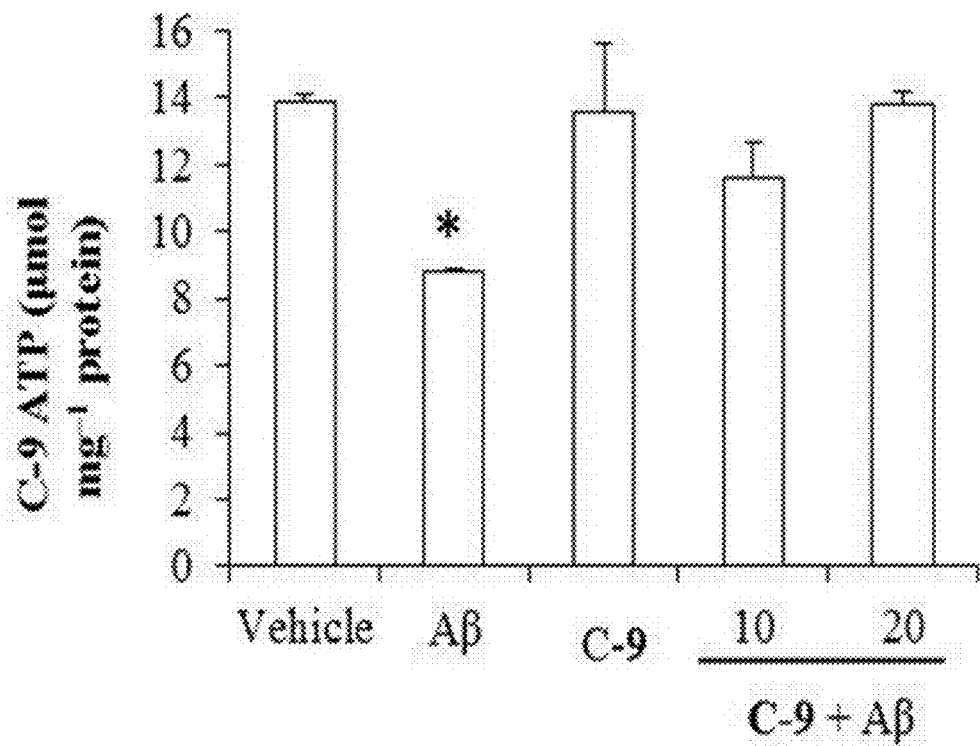
FIG. 5 includes a graph that shows CypD inhibitor Compound 9 revives the Aβ-induced reduction in ATP levels.

The effect of the CypD inhibitors on the levels of adenosine-5'-triphosphate (ATP) was studied. To determine the effect of the CypD inhibitors on Aβ-induced energy metabolism impairment, cellular ATP levels were analyzed. SK-N-SH cells were exposed to 5 μM of $A\beta_{1-42}$ in the presence of 10-20 μM of Compound 9. After 48 hours, we measured the ATP concentrations in the cell lysates. As shown in FIG. 5, $A\beta_{1-42}$ treatment considerably decreased ATP levels, whereas the addition of either CypD inhibitor C Compound 9 rescued ATP concentrations. ATP levels in the cells exposed to CypD inhibitor Compound 9 were comparable to those of vehicle-treated cells without $A\beta_{1-42}$, suggesting no toxic effect of the inhibitors on mitochondrial energy metabolism and ATP production. These data suggest that the synthesized CypD inhibitor Compound 9 prevents mitochondrial dysfunction induced by Aβ.

Figure 6:
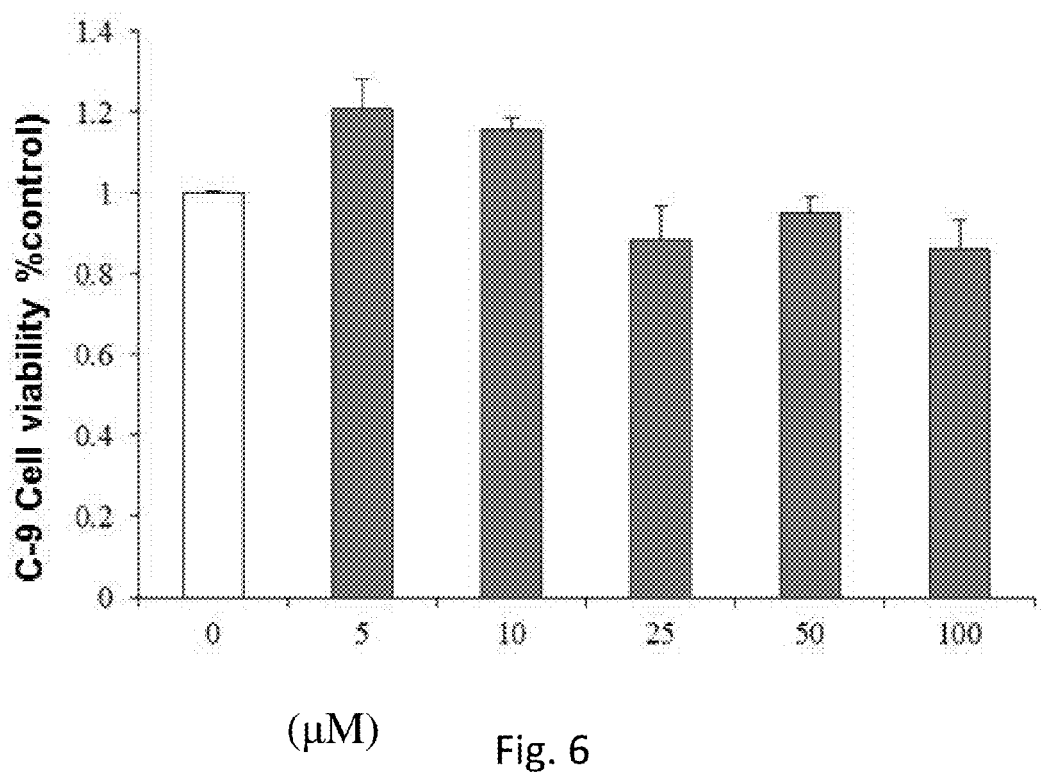
FIG. 6 includes a graph that shows CypD inhibitor Compound 9 has low toxicity.

The effect of the CypD inhibitors on cell viability was studied. Excellent reversal effects of the CypD inhibitor on Aβ-affected processes were observed, including diminished mitochondrial swelling, and enhanced CcO activity and ATP production, assessment of the overall cell health of SK-N-SH cells treated with the CypD inhibitors were studied. A wide dosing range was utilized to examine the effect of the CypD inhibitors on cell viability using an MTT (3-(4,5-dimethylthiazol-2-yl)-2,5-diphenyltetrazolium_bromide) reduction assay (0, 5, 10, 25, 50, and 100 μM of inhibitor diluted in cell culture medium). As is depicted in FIG. 6, the cells exhibited similar reduction of MTT when treated with Compound 9. Also, the increasing dosage of the CypD inhibitor had no significant effect on SK-N-SH cell viability, indicating that inhibitors produce no severe toxic effects at tested doses in healthy cells.

Figure 7:
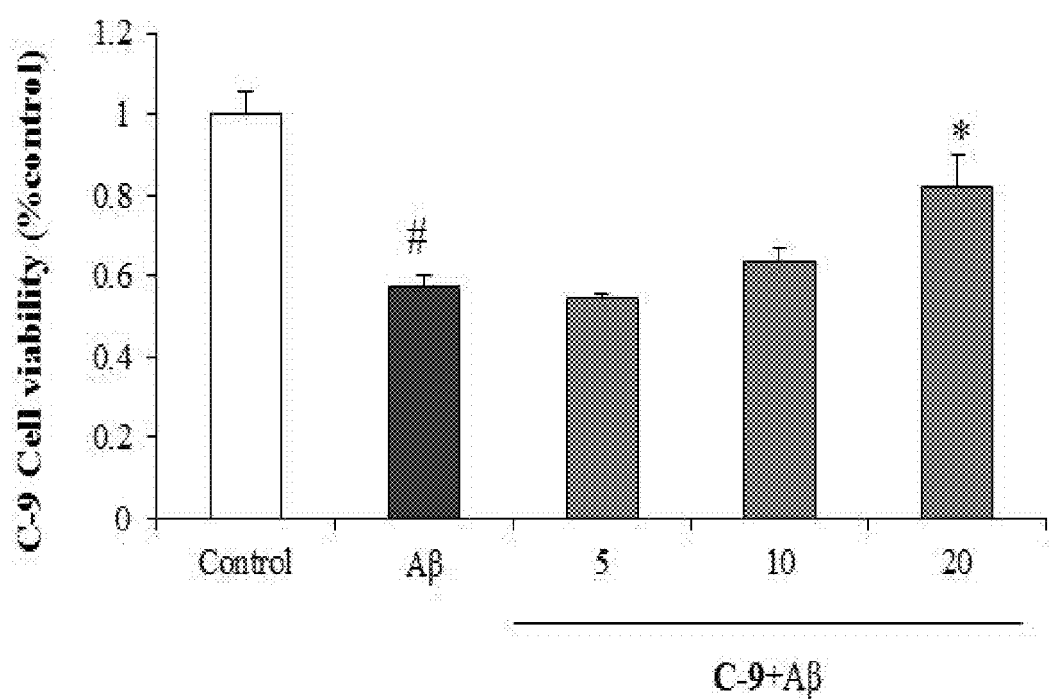
FIG. 7 includes a graph that shows CypD inhibitor Compound 9 inhibits Aβ-induced cell death.

Assays examined the effect of the CypD inhibitor compounds on Aβ-induced neuronal cell death, commonly observed in AD. As demonstrated in FIG. 7, treatment of SK-N-SH cells with $A\beta_{1-42}$ alone resulted in a significant decrease in cell viability as assessed by an MTT reduction assay. The addition of various dosages of inhibitor to the cells in the presence of $A\beta_{1-42}$ increased cell viability. Compound 9 exhibited a significant effect on cell health at both 10 and 20 μM concentrations. These results, in addition to the rescued mitochondrial function data, indicate that CypD inhibitors can reduce the harmful effects of Aβ on neuronal cell health, without producing toxic side effects in unaffected cells. Thus, this evidence provides support that inhibition of CypD with specific inhibitors can provide a beneficial and powerful therapeutic tool in AD treatment.

Figure 12:
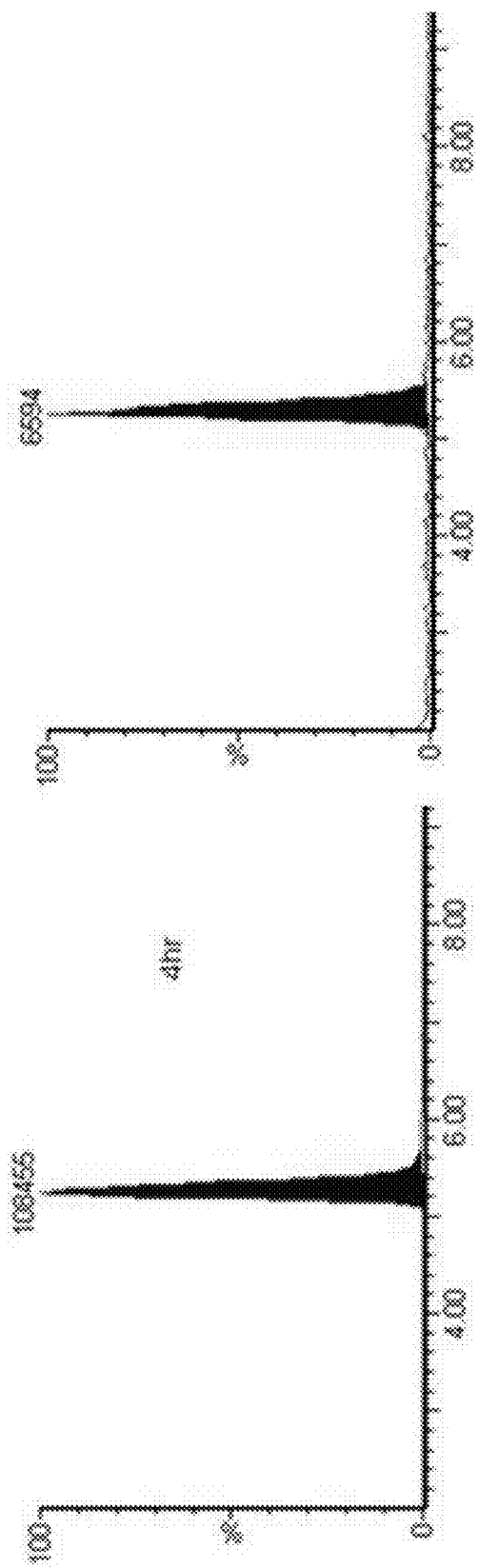
FIG. 12 includes a graph that shows CypD inhibitor Compound 6A crosses the blood brain barrier.
Figure 13:
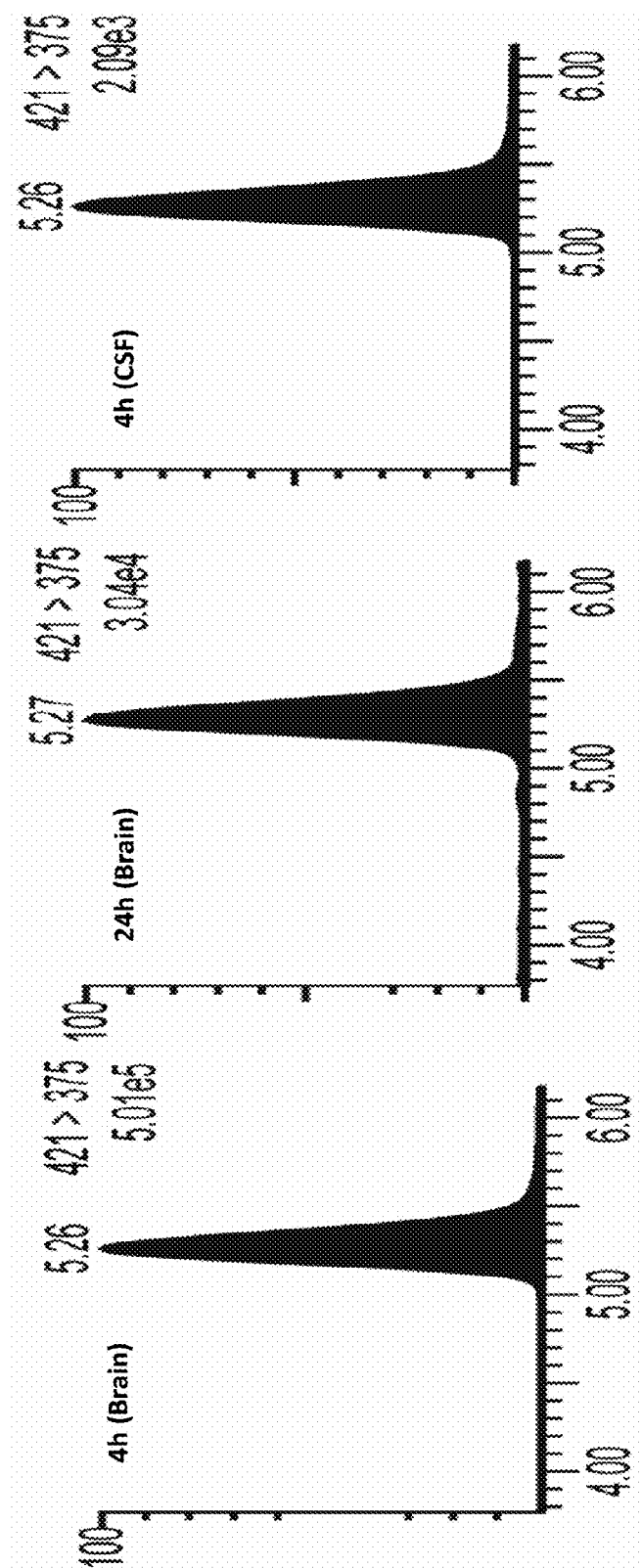
FIG. 13 includes a graph that shows CypD inhibitor Compound 6B crosses the blood brain barrier.
Figure 14:
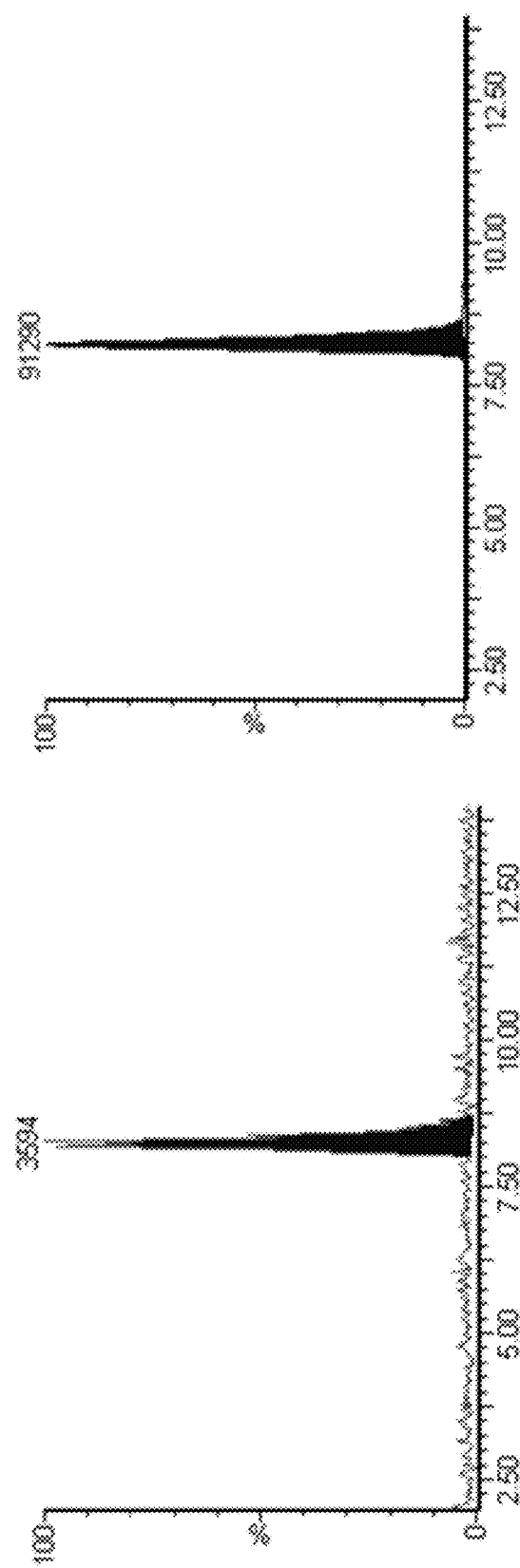
FIG. 14 includes a graph that shows CypD inhibitor Compound 6C crosses the blood brain barrier.

The compounds were shown to be capable of passing the blood brain barrier, which allows for systemic administration into blood or other body fluid that enters the brain for passage into the brain. FIG. 12 shows the representative multiple reaction monitoring (MRM) chromatograms of Compound 6A in CSF and brain. Samples were collected 4 hours after i.v. administration of 10 mg/kg of Compound 6A in mice. FIG. 13 shows the representative multiple reaction monitoring (MRM) chromatograms of Compound 6B in CSF and brain. Samples were collected 4 hours after i.v. administration of 10 mg/kg of Compound 6B in mice. FIG. 14 shows the representative multiple reaction monitoring (MRM) chromatograms of Compound 6C in CSF and brain.

Samples were collected 4 hours after i.v. administration of 10 mg/kg of Compound 6C in mice.

EXPERIMENTAL

Synthesis of CypD Inhibitors

With reference to Scheme 1, Compounds 4a-s were prepared. A solution of ethyl/methyl acetoacetate (1 mmol), urea/thiourea (1 mmol) and ethyl 2-(3-formyl-4-hydroxyphenyl)-4-methylthiazole-5-carboxylate (1 mmol) in ethanol (10 mL) was heated under reflux (78-80° C.) in the presence of polyphosphoric acid (3.3 mol %) for 12 hours under an inert atmosphere. The progress of the reaction was monitored by TLC (hexane:ethyl acetate, 1:1 v/v). After being concentrated under vacuum at 50° C., the reaction mixture was cooled to room temperature, poured into crushed ice (10 g), and stirred for 5-10 min. The solid that separated was filtered under reduced pressure and washed with ice-cold water (20 mL) before recrystallizing from hot ethanol to afford products 4A-4S.

With reference to Scheme 1, Compounds 6a-s were prepared. To a solution of ethyl 6-methyl-4-(3-nitrophenyl)-2-thioxo-1,2,3,4-tetrahydropyrimidine-5-carboxylate (4a) (1 mmol) in ethyl acetate (5 mL), tetrahydrofuran (2.5 mL) and substituted 1-bromo-4-phenyl (1 mmol) were added to this solution, and the reaction mixture was refluxed for 8-12 h at room temperature. The progress of the reaction was monitored by thin layer chromatography (TLC; dichloromethane:ethyl acetate 1:1). Solvent was then removed under reduced pressure to give the crude product which was recrystallized from methanol to give a pure product 6a. Related reactions were used to convert 4b-4s into 6b-6s.

Scheme 1 shows the synthesis for Compounds 4A-4S and Compounds 6A-6S. Table A shows substituents in Scheme 1 for $R^1$, $R^2$, and $R^3$, wherein n is 0 or an integer, such as for example, 0, 1, 2, 3, 4, 5, 6, 7, 8, 9, or 10. Preferably n is 0, 1, or 2. More preferably, n is 0 or 2. Even more preferably, n is 2. Table B shows the structures of Compounds 6A-6S.

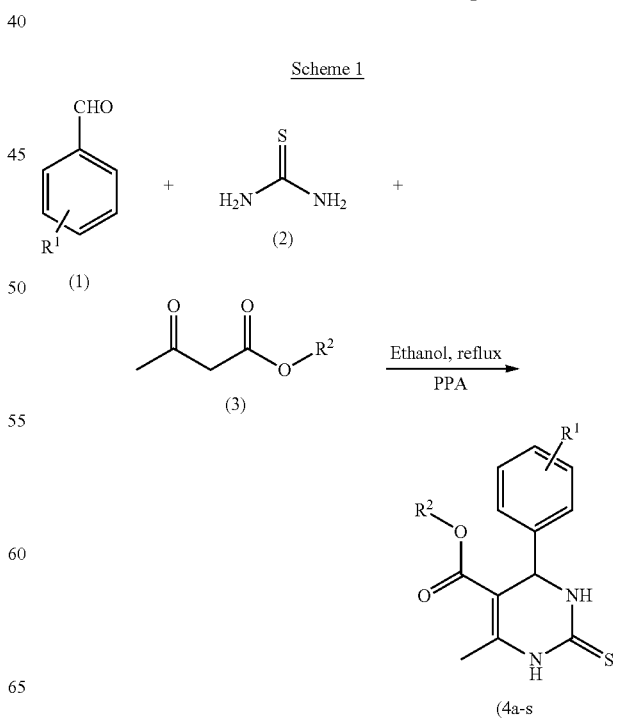

Scheme 1

(4a-s)

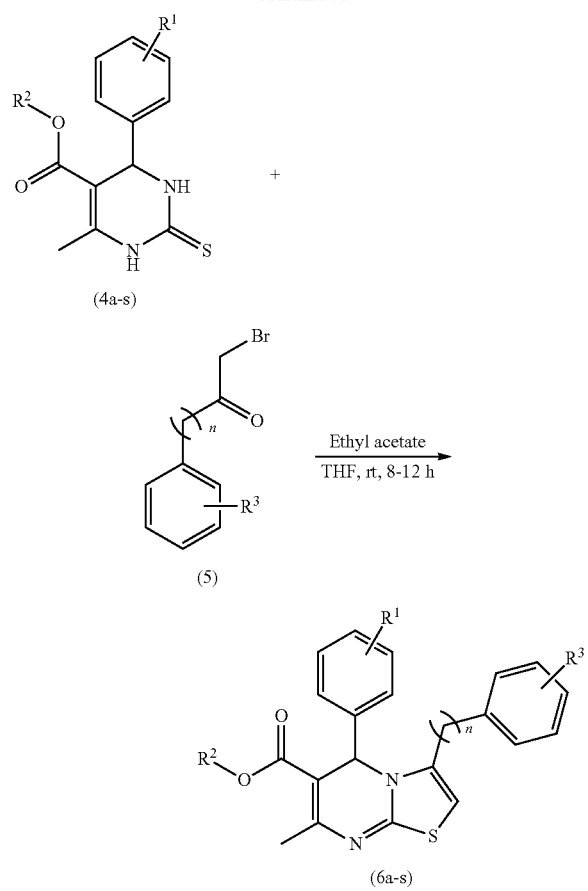
TABLE A
| Entry | R¹ | R³ | R² |
|---|---|---|---|
| 6a | 3-NO₂ | — | Ethyl |
| 6b | 4-OH | — | Ethyl |
| 6c | 4-F | — | Ethyl |
| 6d | 4-OH, 5OOCH₃ | — | Ethyl |
| 6e | 4-OH | — | Methyl |
| 6f | 4-OH, 5OOCH₃ | — | Methyl |
| 6g | 3-NO₂ | 4-OH | Ethyl |
| 6h | 3-NO₂ | 4-F | Ethyl |
| 6i | 3-NO₂ | 3,4-di chloro | Ethyl |
| 6j | 4-OH | 4-OH | Ethyl |
| 6k | 4-OH | 4-F | Ethyl |
| 6l | 4-OH | 3,4-di chloro | Ethyl |
| 6m | 4-F | 4-OH | Ethyl |
| 6n | 4-F | 4-F | Ethyl |
| 6o | 4-F | 3,4-di chloro | Ethyl |
| 6p | 4-OH, 5OOCH₃ | 4-OH | Methyl |
| 6q | 4-OH, 5OOCH₃ | 4-F | Ethyl |
| 6r | 4-OH | 4-OH | Methyl |
| 6s | 4-OH | 4-F | Methyl |
TABLE B
| Compound Numbers | Compound Structures |
|---|---|
| 6A | 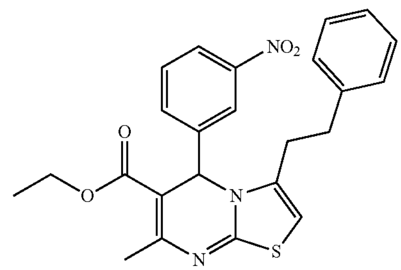 [SMILES: CCOC(=O)C1=C(C)N=C2SC=C(CCc3ccccc3)N2C1c1cccc([N+](=O)[O-])c1] |
| 6B | 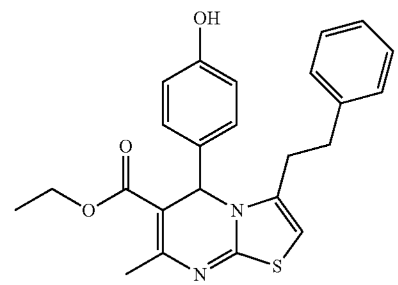 [SMILES: CCOC(=O)C1=C(C)N=C2SC=C(CCc3ccccc3)N2C1c1ccc(O)cc1] |
| 6C | 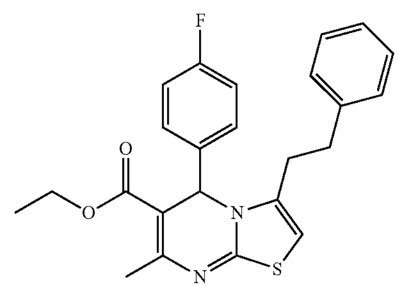 [SMILES: CCOC(=O)C1=C(C)N=C2SC=C(CCc3ccccc3)N2C1c1ccc(F)cc1] |
| 6D | 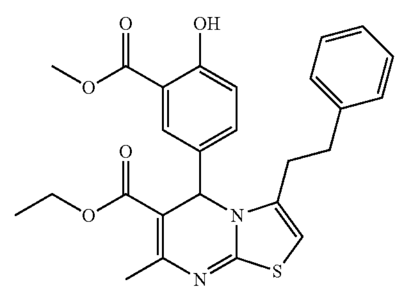 [SMILES: CCOC(=O)C1=C(C)N=C2SC=C(CCc3ccccc3)N2C1c1ccc(O)c(C(=O)OC)c1] |
| 6E | 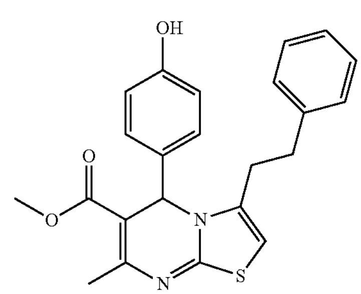 [SMILES: COC(=O)C1=C(C)N=C2SC=C(CCc3ccccc3)N2C1c1ccc(O)cc1] |

TABLE B-continued
| Compound Numbers | Compound Structures |
|---|---|
| 6F | 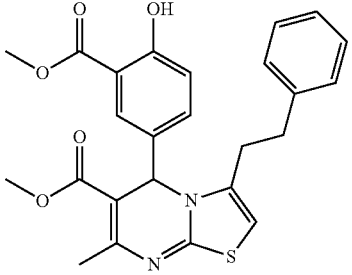 [SMILES: COC(=O)C1=C(C)N=C2SC=C(CCc3ccccc3)N2C1c1ccc(O)c(C(=O)OC)c1] |
| 6G | 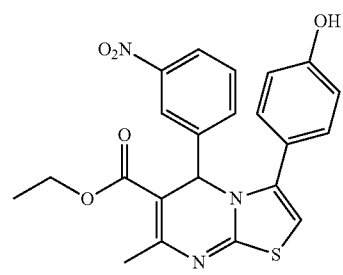 [SMILES: CCOC(=O)C1=C(C)N=C2SC=C(c3ccc(O)cc3)N2C1c1cccc([N+](=O)[O-])c1] |
| 6H | 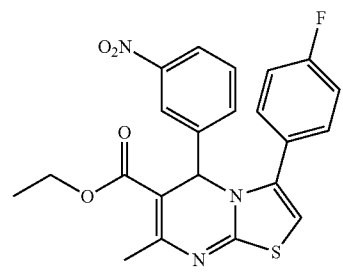 [SMILES: CCOC(=O)C1=C(C)N=C2SC=C(c3ccc(F)cc3)N2C1c1cccc([N+](=O)[O-])c1] |
| 6I | 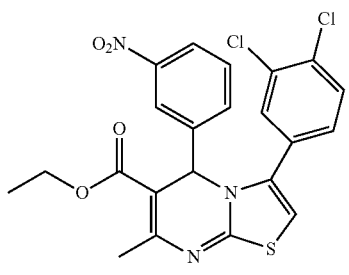 [SMILES: CCOC(=O)C1=C(C)N=C2SC=C(c3ccc(Cl)c(Cl)c3)N2C1c1cccc([N+](=O)[O-])c1] |
| 6J | 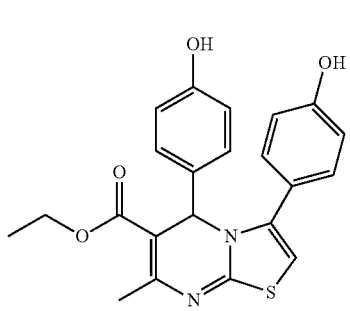 [SMILES: CCOC(=O)C1=C(C)N=C2SC=C(c3ccc(O)cc3)N2C1c1ccc(O)cc1] |
| 6K | 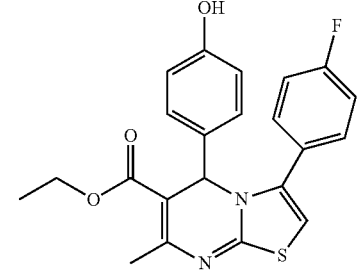 [SMILES: CCOC(=O)C1=C(C)N=C2SC=C(c3ccc(F)cc3)N2C1c1ccc(O)cc1] |
| 6L | 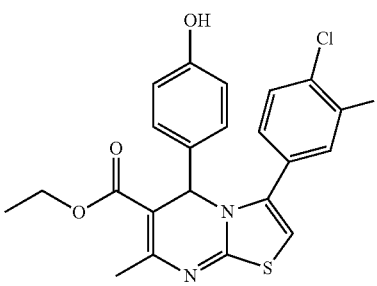 |
| 6M | 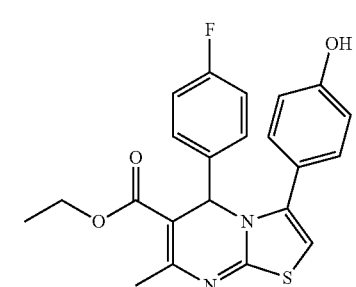 |
| 6N | 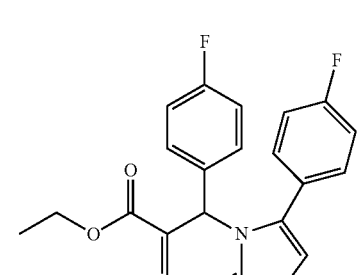 |
| 6O | 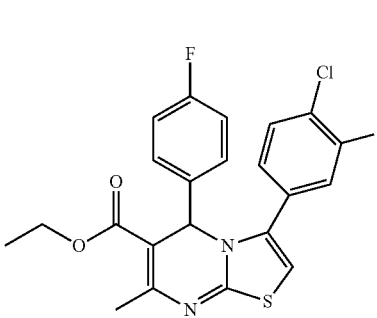 |

TABLE B-continued

| Compound Numbers | Compound Structures |
|---|---|
| 6P | (structure) |
| 6Q | (structure) |
| 6R | (structure) |
| 6S | (structure) |

In reference to Scheme 2, Compound 9 was synthesized. A solution of 2-(3-cyano-4-isobutoxyphenyl)-4-methylthiazole-5-carboxylic acid and thionyl chloride was stirred in dry toluene for 30 min in the presence of a catalytic amount of dimethylformamide to produce an acid chloride intermediate for Compound 9. Slowly increasing the temperature to 90-95° C. with constant stirring for 3 hours resulted in a clear solution. The reaction mixture was then cooled slowly to room temperature and concentrated to give a white residue. This residue was dissolved in acetonitrile and an equimolar amount of 4-aminobenzenesulfonamide was added. This solution was stirred for 4 hours at 75° C. to give impure solid Compound 9. This solid that was separated by filtration, washed with acetonitrile, washed with ice-cold water and then recrystallized from ethanol to give pure C-9. Compound 9 was present as an off-white powder with a melting point of 297-299° C., a molecular weight of 471 and a molecular formula of $C_{22}H_{22}N_4O_4S_2$. High pressure liquid chromatography (HPLC) purity of compound C-9 was 100%.

Scheme 2 shows the synthesis for Compound 9, and can be applied for synthesis for the C-9 Family. Table C shows Compounds 9, 9A, 9B, and 9C.

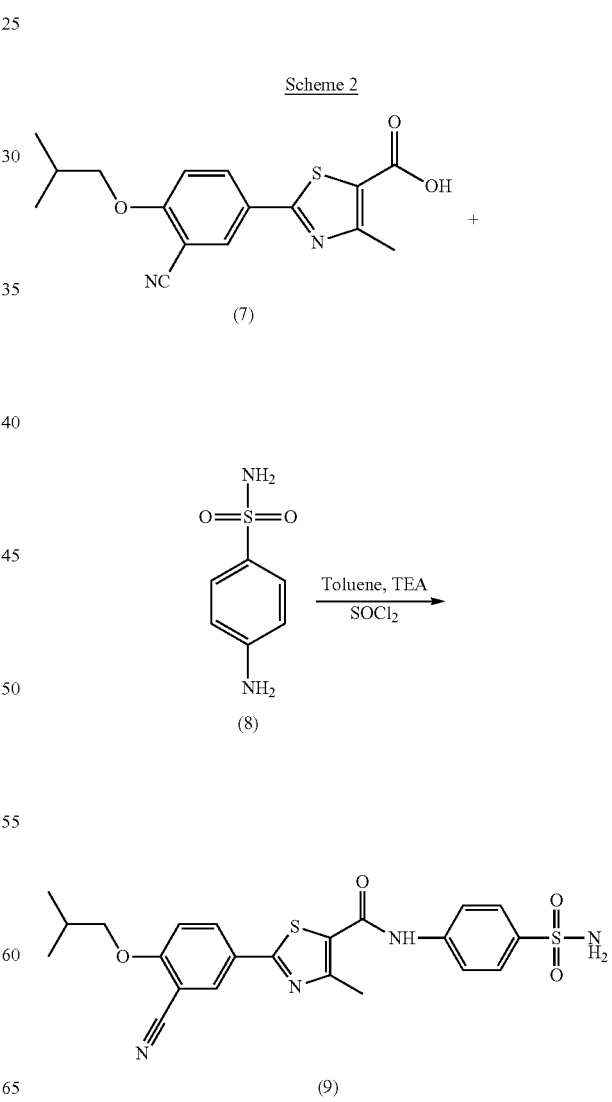

Scheme 2

TABLE C

| Compound Numbers | Compound Structures |
|---|---|
| 9 | 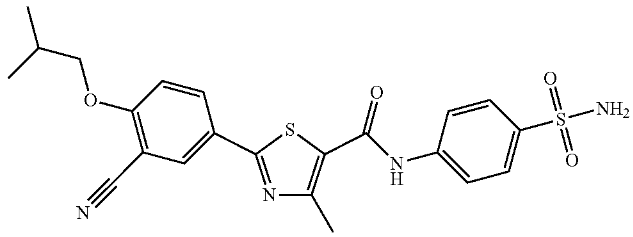 [SMILES: Cc1nc(-c2ccc(OCC(C)C)c(C#N)c2)sc1C(=O)Nc1ccc(S(N)(=O)=O)cc1] |
| 9A | 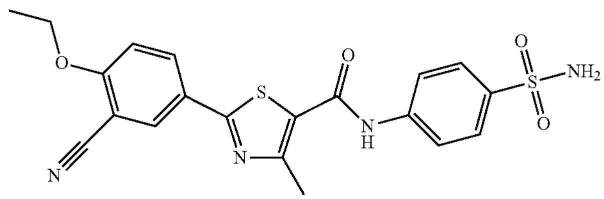 [SMILES: CCOc1ccc(-c2nc(C)c(C(=O)Nc3ccc(S(N)(=O)=O)cc3)s2)cc1C#N] |
| 9B | 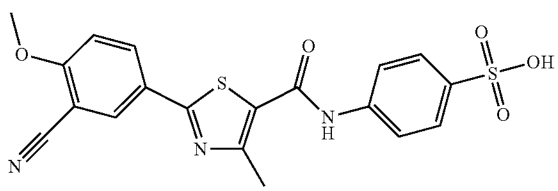 [SMILES: COc1ccc(-c2nc(C)c(C(=O)Nc3ccc(S(=O)(=O)O)cc3)s2)cc1C#N] |
| 9C | 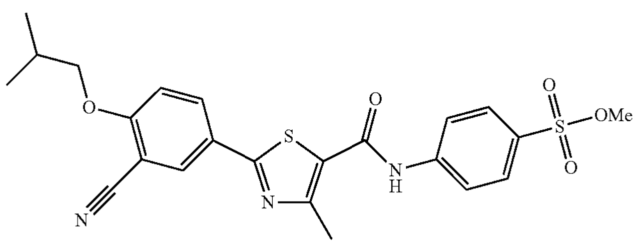 [SMILES: COS(=O)(=O)c1ccc(NC(=O)c2sc(-c3ccc(OCC(C)C)c(C#N)c3)nc2C)cc1] |

The compounds were tested for biological activity. All the synthesized small-molecule Cyclophilin D (CypD) inhibitors bind strongly to CypD and attenuate mitochondrial and cellular perturbation insulted by Aβ and calcium stress. In vitro surface plasmon resonance studies were used to determine binding affinities for the newly synthesized CypD compounds. Compounds 6A, 6B, 6C & 9 were shown to be effective in reducing CypD peptidyl prolyl isomerase enzyme activity. Importantly, these compounds (Compounds 6A, 6B, 6C & 9) also abolished Aβ-induced mitochondrial dysfunction as shown by increased cytochrome c oxidase and adenosine-5'-triphosphate levels.

Additionally a selective and sensitive method for detecting the presence of four compounds (Compounds 6A, 6B, 6C & 9) as CypD inhibitors in mouse plasma, brain and artificial cerebrospinal fluid is based on high performance liquid chromatography tandem mass spectrometry. Mass spectra were generated using Micromass Quattro Ultima "triple" quadrupole mass spectrometer equipped with Electrospray ionization interface. The method used for pharmacokinetic studies of compounds in mouse cerebrospinal fluid, plasma, and brain is accurate, precise, and specific with no matrix effect. Pharmacokinetic data showed these compounds penetrate the blood-brain barrier (BBB) from a 10 mg/kg dose, such as shown in FIGS. 12, 13, and 14. These results indicate that these small molecule CypD inhibitors have good drug properties with the ability to cross the blood brain barrier, which holds a great potential for AD therapy.

The compounds can be substituted with substituents of any of the chemical moieties described herein, such as those recited below.

The term "alkyl" or "aliphatic" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl, and the like. Generally, although again not necessarily, alkyl groups herein contain 1 to about 18 carbon atoms, or 1 to about 12 carbon atoms. The term "lower alkyl" intends an alkyl group of 1 to 6 carbon atoms. Substituents identified as "$C_1$-$C_6$ alkyl" or "lower alkyl" contains 1 to 3 carbon atoms, and such substituents contain 1 or 2 carbon atoms (i.e., methyl and ethyl). "Substituted alkyl" refers to alkyl substituted with one or more substituent groups, and the terms "heteroatom-containing alkyl" and "heteroalkyl" refer to alkyl in which at least one carbon atom is replaced with a heteroatom, as described in further detail infra. If not otherwise indicated, the terms "alkyl" and "lower alkyl" include linear, branched, cyclic, unsubstituted, substituted, and/or heteroatom-containing alkyl or lower alkyl, respectively.

The terms "alkenyl" as used herein refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Generally, although again not necessarily, alkenyl groups herein contain 2 to about 18 carbon atoms, or 2 to 12 carbon atoms. The term "lower alkenyl" intends an alkenyl group of 2 to 6 carbon atoms, and the specific term "cycloalkenyl" intends a cyclic alkenyl group, or having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" as used herein refers to a linear or branched hydrocarbon group of 2 to 24 carbon atoms containing at least one triple bond, such as ethynyl, n-propynyl, and the like. Generally, although again not necessarily, alkynyl groups herein contain 2 to about 18 carbon atoms, or 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Substituents identified as "$C_1$-$C_6$ alkoxy" or "lower alkoxy" herein contain 1 to 3 carbon atoms, and such substituents contain 1 or 2 carbon atoms (i.e., methoxy and ethoxy).

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Examples of aryl groups contain 6 to 20 carbon atoms, and aryl groups contain 6 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituent, in which at least one carbon atom is replaced with a heteroatom, as will be described in further detail infra. If not otherwise indicated, the term "aryl" includes unsubstituted, substituted, and/or heteroatom-containing aromatic substituents.

The term "aryloxy" as used herein refers to an aryl group bound through a single, terminal ether linkage, wherein "aryl" is as defined above. An "aryloxy" group may be represented as —O-aryl where aryl is as defined above. Examples of aryloxy groups contain 5 to 20 carbon atoms, and aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Examples of aralkyl groups contain 6 to 24 carbon atoms, and aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethyinaphthyl, 7-cyclooctylnaphthyl, 3-ethyl-cyclopenta-1,4-diene, and the like.

The term "cyclic" refers to alicyclic or aromatic substituents that may or may not be substituted and/or heteroatom containing, and that may be monocyclic, bicyclic, or polycyclic.

The terms "halo" and "halogen" are used in the conventional sense to refer to a chloro, bromo, and fluoro or iodo substituent.

The term "heteroatom-containing" as in a "heteroatom-containing alkyl group" (also termed a "heteroalkyl" group) or a "heteroatom-containing aryl group" (also termed a "heteroaryl" group) refers to a molecule, linkage or substituent in which one or more carbon atoms are replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

The term "hydrocarbyl" refers to univalent hydrocarbyl radicals containing 1 to about 30 carbon atoms, or 1 to about 24 carbon atoms, or 1 to about 18 carbon atoms, or about 1 to 12 carbon atoms, including linear, branched, cyclic, saturated, and unsaturated species, such as alkyl groups, alkenyl groups, aryl groups, and the like. "Substituted hydrocarbyl" refers to hydrocarbyl substituted with one or more substituent groups, and the term "heteroatom-containing hydrocarbyl" refers to hydrocarbyl in which at least one carbon atom is replaced with a heteroatom. Unless otherwise indicated, the term "hydrocarbyl" is to be interpreted as including substituted and/or heteroatom-containing hydrocarbyl moieties.

By "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, heteroatom-containing alkenyl, and heteroatom-containing aryl."

All other chemistry terms are defined as known in the art.

The reference to Compound 6A (i.e., Compound 6a) herein is identified as compound 6n in the provisional and the publication (Structure Based Design, Synthesis, Pharmacophore Modeling, Virtual Screening, and Molecular Docking Studies for Identification of Novel Cyclophilin D Inhibitors; Koteswara Rao Valasani, † Jhansi Rani Vangavaragu, † Victor W. Day, ‡ and Shirley ShiDu Yan*, ‡. Chem. Inf. Model. 2014, 54, 902-912)), Compound 6B (i.e., Compound 6b) herein is identified as compound 6o in the provisional and publication, and Compound 6C (i.e., Compound 6c) herein is identified as compound 6p in the provisional and publication, and Compound C-9 the same as Compound 9 in the provisional and herein and used interchangeably.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B." In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

All references recited herein are incorporated herein by specific reference in their entirety.

The invention claimed is:

1. A compound of a structure of Formula 1A, salt thereof, or stereoisomer thereof, or tautomer, polymorph, solvate, or combination thereof:

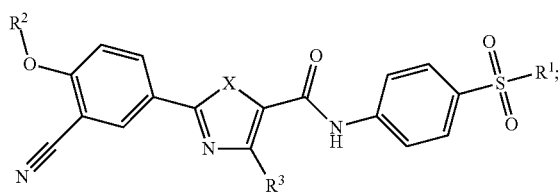

Formula 1A wherein $R^1$, $R^2$, and/or $R^3$ are independently any substituent; and X is S or O.

2. The compound of claim 1, wherein $R^1$, $R^2$, and/or $R^3$ are independently hydrogen, alkyl, alkenyl, alkynyl, aryl, alkaryl, aralkyl, halo, hydroxyl, sulfhydryl, alkoxy, alkenyloxy, alkynyloxy, aryloxy, acyl, alkylcarbonyl, arylcarbonyl, acyloxy, alkoxycarbonyl, aryloxycarbonyl, halocarbonyl, alkylcarbonato, arylcarbonato, carboxy, carboxylato, carbamoyl, mono-(alkyl)-substituted carbamoyl, di-(alkyl)-substituted carbamoyl, mono-substituted aryl carbamoyl, thiocarbamoyl, carbamido, cyano, isocyano, cyanato, isocyanato, isothiocyanato, azido, formyl, thioformyl, amino, mono- and di-(alkyl)-substituted amino, mono- and di-(aryl)-substituted amino, alkylamido arylamido, imino, alkylimino, arylimino, nitro, nitroso, sulfo, sulfonato, alkylsulfanyl, arylsulfanyl, alkylsulfinyl, arylsulfinyl, alkyl sulfonyl, aryl sulfonyl, phosphono, phosphonato, phosphinato, phospho, phosphino, any with or without hetero atoms substituting one or more carbons in a chain or ring or added to a chain or ring, and combinations thereof.

3. The compound of claim 1, wherein the compound has $R^1$ is an amino.

4. The compound of claim 3, wherein the compound has the structure of Compound 9:

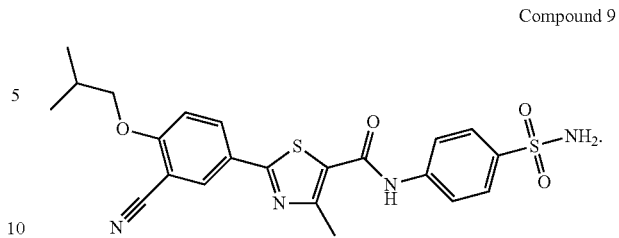

Compound 9

5. The compound of claim 3, wherein the compound has the structure of Compound 9A:

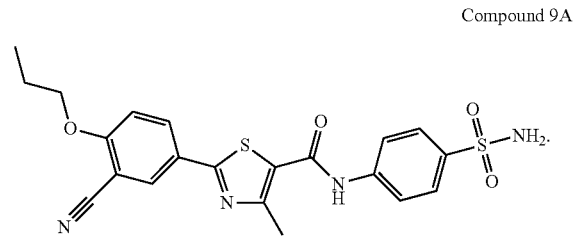 [SMILES: CCCOc1ccc(-c2nc(C)c(C(=O)Nc3ccc(S(N)(=O)=O)cc3)s2)cc1C#N]

Compound 9A

6. The compound of claim 1, wherein the compound has the structure of Compound 9B:

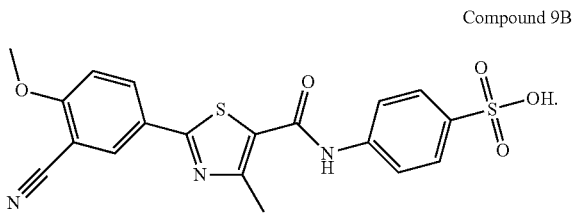 [SMILES: COc1ccc(-c2nc(C)c(C(=O)Nc3ccc(S(=O)(=O)O)cc3)s2)cc1C#N]

Compound 9B

7. The compound of claim 1, wherein the compound has the structure of Compound 9C:

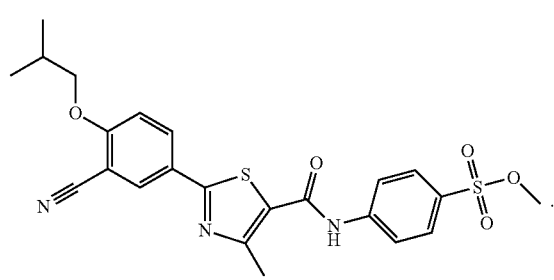

Compound 9C

8. A pharmaceutical composition comprising:
a compound of claim 1; and
a pharmaceutically acceptable carrier.

9. A method of inhibiting Cyclophilin D, comprising:
providing a compound of claim 1; and
administering the compound to Cyclophilin D.

10. A method of rescuing Aβ-mediated mitochondrial dysfunction, comprising:
providing a compound of claim 1; and
administering the compound to Cyclophilin D.

11. The compound of claim 1, wherein $R^2$ is an alkyl.

12. The compound of claim 1, wherein $R^3$ is an alkyl.

13. The compound of claim 1, with $R^1$ being a straight or branched alkyl or aryl substituted or unsubstituted, alkoxy, amino or hydroxyl, $R^2$ being a straight or branched alkyl or aryl substituted or unsubstituted, and $R^3$ being a straight or branched alkyl or aryl substituted or unsubstituted.

14. The compound of claim 1, wherein $R^1$ is an amino, $R^2$ is a straight or branched alkyl, and $R^3$ is a methyl.

15. The compound of claim 1, with $R^2$ being a methyl, ethyl, or propyl.

* * * * *